US011497746B2

(12) United States Patent
Quayle et al.

(10) Patent No.: US 11,497,746 B2
(45) Date of Patent: Nov. 15, 2022

(54) PHARMACEUTICAL COMBINATIONS COMPRISING A HISTONE DEACETYLASE INHIBITOR AND A PROGRAMMED DEATH-LIGAND 1 (PD-L1) INHIBITOR AND METHODS OF USE THEREOF

(71) Applicant: Acetylon Pharmaceuticals, Inc., Boston, MA (US)

(72) Inventors: Steven Norman Quayle, Brookline, MA (US); Simon Stewart Jones, Harvard, MA (US); Teru Hideshima, Brookline, MA (US); Kenneth C. Anderson, Wellesley, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 32 days.

(21) Appl. No.: 16/463,140

(22) PCT Filed: Nov. 21, 2017

(86) PCT No.: PCT/US2017/062822
§ 371 (c)(1),
(2) Date: May 22, 2019

(87) PCT Pub. No.: WO2018/098168
PCT Pub. Date: May 31, 2018

(65) Prior Publication Data
US 2019/0282573 A1  Sep. 19, 2019

Related U.S. Application Data

(60) Provisional application No. 62/425,885, filed on Nov. 23, 2016.

(51) Int. Cl.
*A61K 31/505* (2006.01)
*A61K 39/395* (2006.01)
(Continued)

(52) U.S. Cl.
CPC .......... *A61K 31/505* (2013.01); *A61K 31/454* (2013.01); *A61K 31/573* (2013.01);
(Continued)

(58) Field of Classification Search
CPC .. A61K 31/505; A61K 39/39558; A61P 35/00
See application file for complete search history.

(56) References Cited

U.S. PATENT DOCUMENTS 8,394,810 B2  3/2013 van Duzer et al.
8,614,223 B2  12/2013 van Duzer et al.
(Continued)

FOREIGN PATENT DOCUMENTS

WO  WO 2015/157162 A1  10/2015
WO  WO 2016/154068     9/2016

OTHER PUBLICATIONS

Ray et al. 652. Myeloma: Pathophysiology and pre-clinical studies excluding therapy: Poster II (Dec. 3, 2015 (Year: 2015).*
(Continued)

*Primary Examiner* — Shengjun Wang
(74) *Attorney, Agent, or Firm* — Brian C. Trinque; Lathrop GPM LLP

(57) ABSTRACT

The present disclosure relates to a pharmaceutical combination comprising (a) a histone deacetylase 6 inhibitor and (b) a programmed death ligand 1 (PD-L1) inhibitor, including combined preparations and pharmaceutical compositions thereof; uses of such combination in the treatment or prevention of cancer; and methods of treating or preventing cancer in a subject comprising administering a therapeutically effective amount of such combination.

3 Claims, 9 Drawing Sheets

Specification includes a Sequence Listing.

(51) Int. Cl.
*A61P 35/00* (2006.01)
*A61K 31/454* (2006.01)
*A61K 31/573* (2006.01)
*C07K 16/28* (2006.01)
*A61K 45/06* (2006.01)
*A61K 39/00* (2006.01)

(52) U.S. Cl.
CPC .............. *A61K 45/06* (2013.01); *A61P 35/00* (2018.01); *C07K 16/2827* (2013.01); *A61K 2039/505* (2013.01); *C07K 2317/732* (2013.01)

(56) References Cited

U.S. PATENT DOCUMENTS

| | | | |
|---|---|---|---|
| 9,278,963 | B2 | 3/2016 | van Duzer et al. |
| 9,403,779 | B2 | 8/2016 | Tamang et al. |
| 9,464,073 | B2 | 10/2016 | Mazitschek et al. |
| 9,663,825 | B2 | 5/2017 | Yang et al. |
| 9,833,466 | B2 | 12/2017 | Jones et al. |
| 9,937,174 | B2 | 4/2018 | Pozzi et al. |
| 9,949,972 | B2 | 4/2018 | Quayle et al. |
| 10,144,714 | B2 | 12/2018 | Seyedi et al. |
| 10,370,324 | B2 | 8/2019 | van Duzer et al. |
| 10,464,906 | B2 | 11/2019 | van Duzer et al. |
| 2013/0225543 | A1 | 8/2013 | Jones et al. |
| 2015/0105358 | A1* | 4/2015 | Quayle ................ A61K 31/454 514/171 |
| 2015/0105383 | A1 | 4/2015 | Quayle et al. |
| 2015/0105409 | A1 | 4/2015 | Quayle et al. |
| 2015/0150871 | A1 | 6/2015 | Quayle et al. |
| 2015/0176076 | A1 | 6/2015 | Yang et al. |
| 2015/0352206 | A1* | 12/2015 | Gajewski ................ A61K 45/06 424/142.1 |
| 2016/0185716 | A1 | 6/2016 | Sotomayor et al. |
| 2018/0036306 | A1 | 2/2018 | Jones et al. |
| 2019/0046529 | A1 | 2/2019 | Quayle et al. |
| 2019/0209559 | A1 | 7/2019 | Jones et al. |
| 2019/0262337 | A1 | 8/2019 | Moore et al. |
| 2019/0321361 | A1 | 10/2019 | Huang et al. |
| 2020/0323848 | A1 | 10/2020 | Wong et al. |

OTHER PUBLICATIONS

Ghebeh et al., "The B7-H1 (PD-L1) T Lymphocyte—Inhibitory Molecule is Expressed in Breast Cancer patients with Infiltrating Ductal Carcinoma: Correlation with Important High-Risk Prognostic Factors", Neoplasia, vol. 8, No. 3, Mar. 2006, pp. 190-198.

International Search Report and Written Opinion in related PCT Application No. PCT/US2017/062822, dated Mar. 19, 2018 (10 pages).

Niesvizky et al. "3307: Selective HDAC6 Inhibitor ACY-241, an Oral Tablet, Combined with Pomalidomide and Dexamethasone: Safety and Efficacy of Escalation and Expansion Cohorts in Patients with Relapsed or Relapsed-and-Refractory Multiple Myeloma (ACE-MM-200 Study)," Blood, Dec. 1, 2016, vol. 128, Iss. 22, p. 3307.

North et al. "Enhancement of pomalidomide anti-tumor response with ACY-241, a selective HDAC6 inhibitor," PLoS ONE, Mar. 6, 2017, vol. 12, Issue 3, e0173507, pp. 1-16.

Ray et al. "328: Combination of a Novel HDAC 6 Inhibitor ACY-241 with Anti-PD-L1 Antibody Enhances Anti-Tumor Immunity and Cytotoxicity in Multiple Myeloma," Blood, Dec. 1, 2016, vol. 128, No. 22, p. 382.

Ray et al. "Combination of a Novel HDAC6 inhibitor ACY-241 with anti-PD-L1 antibody enhances anti-tumor immunity and cytotoxicity in multiple myeloma," Leukemia, Nov. 6, 2017.

* cited by examiner

PHARMACEUTICAL COMBINATIONS COMPRISING A HISTONE DEACETYLASE INHIBITOR AND A PROGRAMMED DEATH-LIGAND 1 (PD-L1) INHIBITOR AND METHODS OF USE THEREOF

CROSS-REFERENCE TO RELATED APPLICATIONS

This application is a 35 U.S.C. § 371 filing of International Application No. PCT/US2017/062822, filed Nov. 21, 2017, which application claims the benefit of U.S. Provisional Application No. 62/425,885, filed Nov. 23, 2016, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 19, 2019, is named 610889-ACT-043US-SEQ-TXT.txt and is 6.824 bytes in size.

BACKGROUND

Histone deacetylase (HDAC) inhibition can cause cancer cell growth arrest. However, pan-HDAC inhibition leads to significant adverse effects, and an alternative HDAC inhibition profile is desirable.

HDAC6 is a class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

In spite of numerous treatment options for cancer patients, there remains a need for effective and safe therapeutic options. In particular, there is a need for effective methods of treating or preventing cancers, especially those cancers that have been resistant and/or refractive to current therapies. This need can be fulfilled by the use of combination therapies such as those described herein.

SUMMARY

Provided herein is a pharmaceutical combination comprising a Histone deacetylase 6 (HDAC6) inhibitor and a programmed death ligand 1 (PD-L1) inhibitor.

In a first aspect, provided herein is a pharmaceutical combination comprising a therapeutically effective amount of a HDAC6 inhibitor, or a pharmaceutically acceptable salt thereof and a PD-L1 inhibitor.

In various embodiments, the combination further comprises a compound selected from thalidomide, or an analog thereof, or a pharmaceutically acceptable salt thereof. In certain embodiments, the compound is selected from thalidomide, pomalidomide, and lenalidomide, or a pharmaceutically acceptable salt thereof. In exemplary embodiments, the compound is pomalidomide.

In various embodiments, the HDAC6 inhibitor is a HDAC6-selective inhibitor. In other embodiments, the HDAC6 inhibitor is a compound of Formula I:

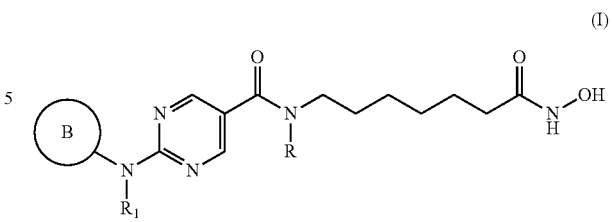

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl.

In various embodiments of the pharmaceutical combination, ring B is aryl.

In various embodiments of the pharmaceutical combination, $R_1$ is aryl or heteroaryl, each of which is substituted by halo.

In various embodiments of the pharmaceutical combination, the HDAC6 inhibitor of Formula I is:

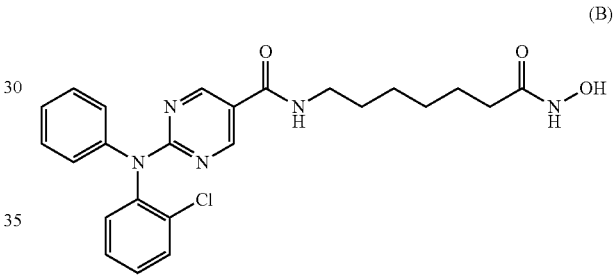

(B)

or a pharmaceutical acceptable salt thereof.

In various embodiments of the pharmaceutical combination, the HDAC6 inhibitor of Formula I is:

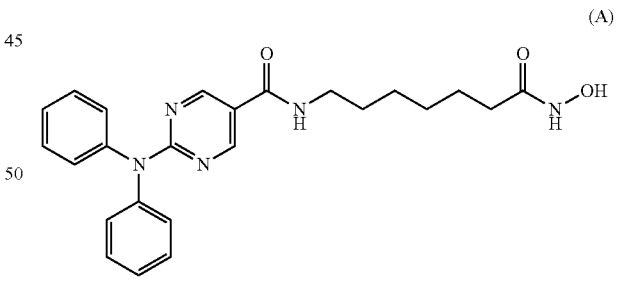

(A)

or a pharmaceutically acceptable salt thereof.

In various embodiments of the pharmaceutical combination, the PD-L1 inhibitor is an inhibitory antibody.

In various embodiments, the inhibitory PD-L1 antibody comprises a heavy chain and a light chain, wherein the heavy chain comprises a variable region comprising three CDRs comprising amino acid sequences within the amino acid sequence of SEQ ID NO.: 1, and wherein the light chain comprises a variable region comprising three CDRs comprising amino acid sequences within the amino acid sequence of SEQ ID NO.: 2. In another embodiment, the PD-L1 inhibitory antibody comprises a heavy chain variable region comprising an amino acid sequence within the amino acid sequence of SEQ ID NO.: 1. In various embodiments, the heavy chain comprises a derivative or a portion of the amino acid sequence of SEQ ID NO.: 1. For example, the heavy chain comprises an amino acid sequence that is 70%, 75%, 80%, 85%, 90%, 95% or 99% identical to the amino acid sequence of SEQ ID NO.: 1. In another embodiment, the PD-L1 inhibitory antibody comprises a light chain variable region comprising an amino acid sequence within the amino acid sequence of SEQ ID NO.: 2. In various embodiments, the light chain comprises a derivative or a portion of the amino acid sequence of SEQ ID NO.: 2. For example, the light chain comprises an amino acid sequence 70%, 75%, 80%, 85%, 90%, 95% or 99% identical to the amino acid sequence of SEQ ID NO.: 2. In another embodiment, the PD-L1 inhibitory antibody comprises a heavy chain comprising the amino acid sequence of SEQ ID NO.: 1, and a light chain comprising the amino acid sequence of SEQ ID NO.: 2.

In various embodiments of the pharmaceutical combination, the HDAC6 inhibitor and the PD-L1 inhibitor are in the same formulation. In other embodiments of the pharmaceutical combination, the HDAC6 inhibitor and the PD-L1 inhibitor are in separate formulations.

In various embodiments of the pharmaceutical combination, the HDAC6 inhibitor is in a formulation for oral administration, and the PD-L1 inhibitor is in a formulation for intravenous administration.

In various embodiments of the pharmaceutical combination, the pharmaceutical combination is used in the treatment of cancer in a subject in need thereof. In another embodiment, the pharmaceutical combination is used for the manufacture of a pharmaceutical preparation or medicament for the treatment of cancer.

In another aspect, provided herein is a method for treating cancer in a subject in need thereof, comprising administering to the subject a therapeutically effective amount of the pharmaceutical combinations provided herein.

In an aspect, provided herein is a method for upregulating antibody-dependent cell-mediated cytotoxicity in a subject in need thereof, comprising administering to the subject a therapeutically effective amount of the pharmaceutical combinations provided herein.

In an aspect, provided herein is a method for upregulating lymphocyte functional activity in a subject in need thereof, comprising administering to the subject a therapeutically effective amount of the pharmaceutical combinations provided herein.

In various embodiments, the lymphocyte is a natural killer cell. In other embodiments, the lymphocyte is a T lymphocyte. In other embodiments, the T lymphocyte is a cytotoxic T lymphocyte.

In various embodiments of the pharmaceutical combinations, the combination further comprises dexamethasone.

In various embodiments of the methods, the method further comprises administering to the subject a therapeutically effective amount of dexamethasone.

DETAILED DESCRIPTION

Figure 1:
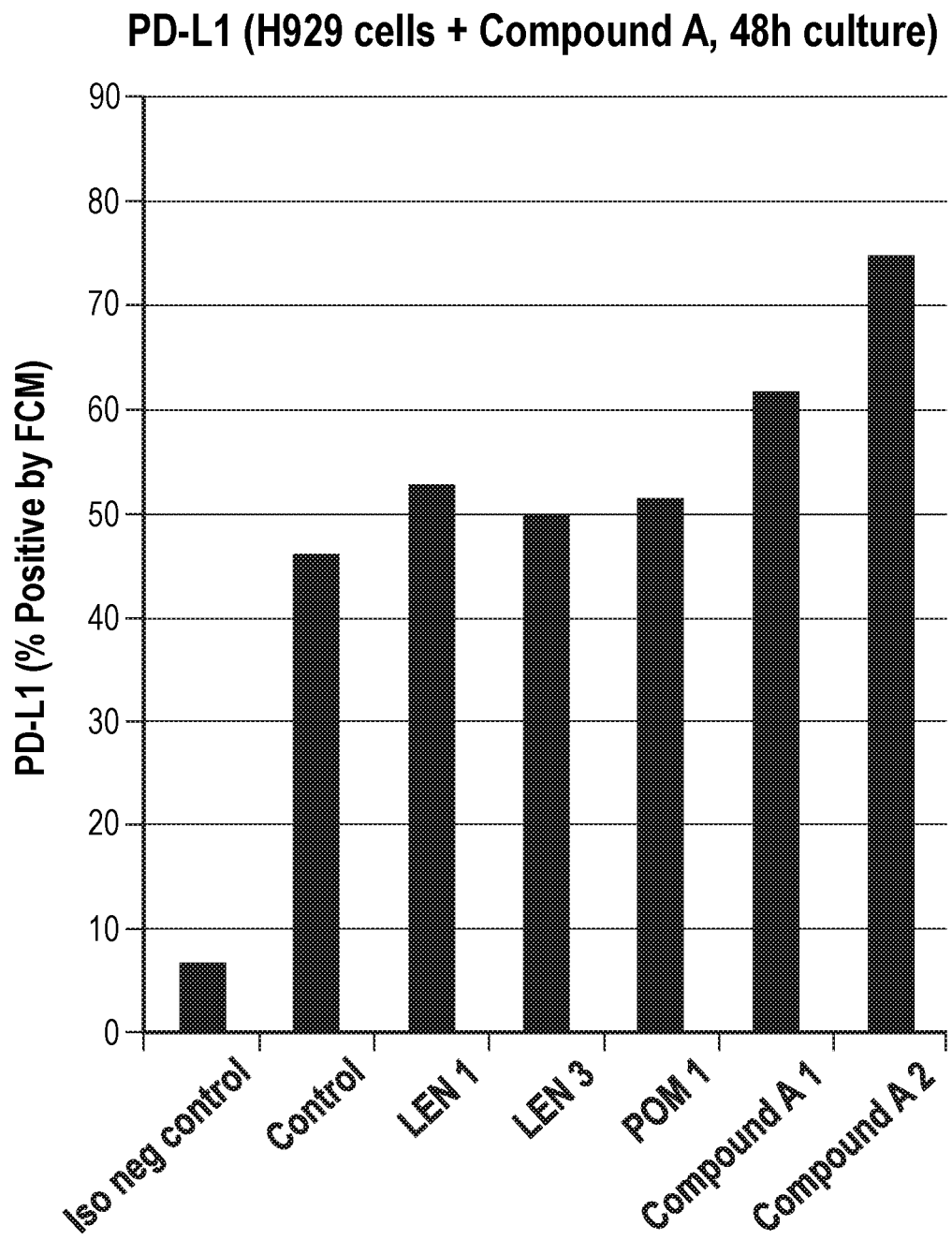
FIG. 1 is a bar graph showing the expression of PD-L1 in myeloma cells cultured for 48 hours with 1 μM of lenalidomide (LEN 1), 3 μM of lenalidomide (LEN 3), 1 μM of pomalidomide (POM 1), 1 μM of Compound A (Compound A1) or 2 μM of Compound A (Compound A2).

Provided herein is a pharmaceutical combination comprising a histone deacetylase inhibitor (HDAC) inhibitor and a programmed death ligand 1 (PD-L1) inhibitor. Specifically, provided herein is a pharmaceutical combination comprising:

(a) a HDAC6 inhibitor of Formula I:

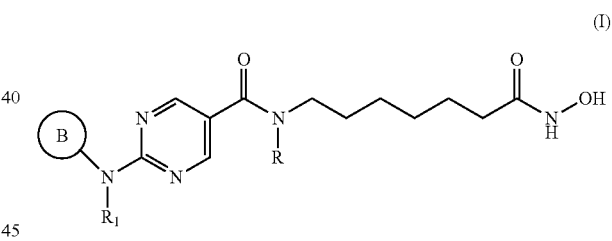

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl; and (b) a PD-L1 inhibitor, or a pharmaceutically acceptable salt thereof.

Definitions

Certain terms used herein are described below. Compounds of the present invention are described using standard nomenclature. Unless defined otherwise, all technical and scientific terms used herein have the same meaning as is commonly understood by one of skill in the art to which this invention belongs.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties. The number of carbon atoms in an alkyl substituent can be indicated by the prefix "$C_{x-y}$," where x is the minimum and y is the maximum number of carbon atoms in the substituent.

As used herein, the term "halo" or "halogen" alone or as part of another substituent means, unless otherwise stated, a fluorine, chlorine, bromine, or iodine atom, preferably, fluorine, chlorine, or bromine, more preferably, chlorine.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like. In an embodiment, $C_4$-$C_7$ heteroaryl groups are provided herein.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The term "pharmaceutically acceptable" as used herein refers to those compounds, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination," "fixed dose," and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that the active ingredients, i.e., the HDAC6 inhibitor and the PD-L1 inhibitor, are administered to a patient as separate entities either simultaneously, concurrently or sequentially with no specific time limits, wherein such administration provides therapeutically effective levels of the two compounds in the body of the subject in need thereof. The latter also applies to cocktail therapy, e.g., the administration of three or more active ingredients.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer.

The term "prevent," "preventing," or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

The term "synergistic effect" as used herein, refers to action of two agents such as, for example, a compound of Formula I (e.g., Compound B), or a pharmaceutically acceptable salt thereof, and a PD-L1 inhibitor (e.g., MDX-1105), to produce an effect, for example, slowing the symptomatic progression of cancer or symptoms thereof, which is greater than the simple addition of the effects of each drug administered by itself. A synergistic effect can be calculated, for example, using suitable methods such as the Sigmoid-Emax equation (Holford, N. H. G. and Scheiner, L. B., Clin.

Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

As used herein, the term "resistant" or "refractive" to a therapeutic agent when referring to a cancer patient means that the cancer has innate, or achieved resistance to, the effects of the therapeutic agent as a result of contact with the therapeutic agent. Stated alternatively, the cancer is resistant to the ordinary standard of care associated with the particular therapeutic agent.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value. The term "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The term "histone deacetylase" or "HDAC" refers to enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "histone deacetylase inhibitor" (HDAC inhibitors, HDACi, HDIs) as used herein refers to a compound that selectively targets, decreases, or inhibits at least one activity of a histone deacetylase.

Histone Deacetylase Inhibitors

Provided herein are pharmaceutical combinations comprising a HDAC6 inhibitor of Formula I (also referred to herein as "compounds of Formula I"):

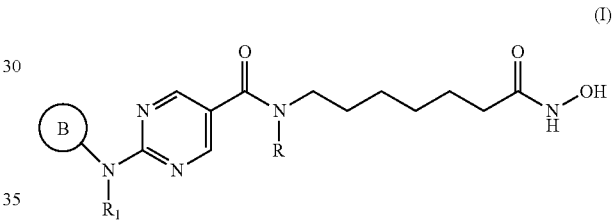

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl.

In various embodiments of the compound of Formula I, ring B is aryl. In various embodiments of the compound of Formula I, $R_1$ is aryl or heteroaryl, each of which is substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by halo.

In yet another embodiment of Formula I, $R_1$ is phenyl that is substituted by chloro.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In a specific embodiment, the compound of Formula I is Compound A, or a pharmaceutically acceptable salt thereof, or Compound B, or a pharmaceutically acceptable salt thereof, as shown in Table 1:

TABLE 1

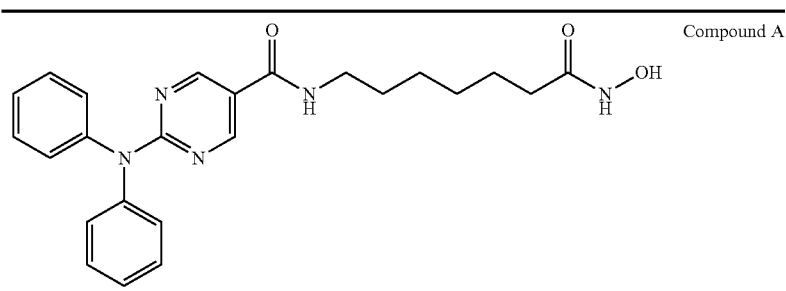

2-(diphenylamino)-N-(7-(hydroxyamino)-7-
oxoheptyl)pyrimidine-5-carboxamide
$IC_{50}$(nM) HDAC6 = 10 HDAC3 = 84

Compound A

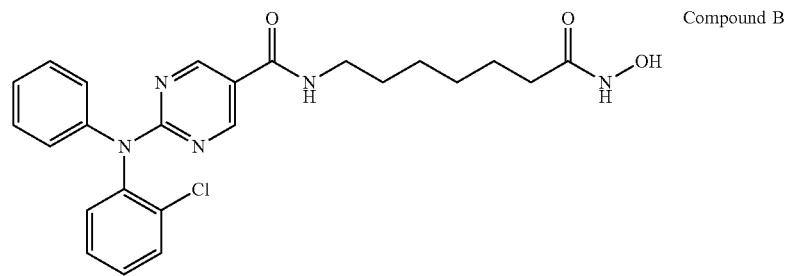

2-((2-chlorophenyl)(phenyl)amino)-N-(7-
(hydroxyamino)-7-oxoheptyl)pyrimidine-5-
carboxamide
$IC_{50}$(nM) HDAC6 = 4 HDAC3 = 76

Compound B

For convenience, the group of the HDAC6 inhibitors of Formula I and its salts are collectively referred to to as compounds of Formula I, meaning that reference to compounds of Formula I will refer to any of the compounds or pharmaceutically acceptable salts thereof in the alternative.

Compounds of Formula I (e.g., Compounds A and B) are known HDAC6 inhibitors, and are described in PCT Pub. No. WO2011/091213, the content of which is incorporated herein by reference in its entirety.

The preparation of Compounds A and B are also described herein as Example 1. Preferably, Compounds A and B are in the free base form.

PD-L1 Inhibitors

The term "programmed death ligand 1 (PD-L1) inhibitor" as used herein refers to a compound that selectively targets, decreases, or inhibits at least one activity of PD-L1. Disorders associated with dysregulated PD-L1 are, e.g., solid tumor cancers including, but not limited to, lung cancer, breast and ovarian cancers, pancreatic and esophagus adenocarcinoma, renal and bladder cancer, head and neck cancer, melanoma, as well as hematological cancers including leukemia and lymphomas (e.g., AML, ALL, and CML) (Ghebeh et al., Neoplasia, 8(3):190-8, 2006 March).

Non-limiting examples of PD-L1 inhibitors include e.g., atezolizumab (MPDL3280), avelumab (MSB0010718C), durvalumab (MEDI-4736), and MDX-1105 (BMS-936559), or pharmaceutically acceptable salts thereof. Any of these PD-L1 inhibitors can be used in the pharmaceutical combinations provided herein.

Accordingly, in various embodiments of the pharmaceutical combination, the PD-L1 inhibitor is selected from the group consisting of atezolizumab (MPDL3280), avelumab (MSB0010718C), MDX-1105 (BMS-936559), and durvalumab (MEDI-4736), or pharmaceutically acceptable salts thereof. In an embodiment of the pharmaceutical combination, the PD-L1 inhibitor is atezolizumab. In an embodiment of the pharmaceutical combination, the PD-L1 inhibitor is avelumab. In an embodiment of the pharmaceutical combination, the PD-L1 inhibitor is durvalumab. In an exemplary embodiment of the pharmaceutical combination, MDX-1105 is used. The amino acid sequences of MDX-1105 heavy chain and light chain are shown in Table 2.

TABLE 2

Sequence of Selected Anti-PD-L1 Antibody

| Protein | Sequence Identifier | Sequence |
|---|---|---|
| MDX-1105 Heavy Chain | SEQ ID NO.: 1 | QVQLVQSGAEVKKPGSSVKVSCKTS GDTFSTYAISWVRGAPGQGLEWMGG IIPIFGKAHYAQKFQGRVTITADES TSTAYMELSSLRSEDTAVYFCARKF HFVSGSPFGNDVQGQGTTVTVSSAS TKGPSVFPLAPCSRSTSESTAALGC LVKDYFPEPVTVSWNSGALTSGVHT FPAVLQSSGLYSLSSVVTVPSSSLG TKTYTCNVDHKPSNTKVDKRVESKY GPPCPPCPAPEFLGGPSVFLFPPKP KDTLMISRTPEVTCVVVDVSQEDPE VQFNWYVDGVEVHNAKTKPREEQFN STYRVVSVLTVLHQDWLNGKEYKCK VSNKGLPSSIEKTISKAKGQPREPQ VYTLPPSQEEMTKNQVSLTCLVKGF YPSDIAVEWESNGQPENNYKTTPPV LDSDGSFFLYSRLTVDKSRWQEGNV FSCSVMHEALHNHYTQKSLSLSLGK |

TABLE 2-continued

Sequence of Selected Anti-PD-L1 Antibody

| Protein | Sequence Identifier | Sequence |
|---|---|---|
| MDX-1105 Light Chain | SEQ ID NO.: 2 | EIVLTQSPATLSLSPGERATLSCRA SQSVSSYLVWYQQKPGQAPRLLIYD ASNRATGIPARFSGSGSGTDFTLTI SSLEPEDFAVYYCQQRSNWPRTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC |

In various embodiments of the pharmaceutical combination, the PD-L1 inhibitor is a derivative, or a portion of any of the antibodies described herein (e.g., atezolizumab, avelumab, durvalumab and the MDX-1105 anti-PD-L1 antibody in Table 2). For example, the PD-L1 inhibitor is a derivative or fragment of atezolizumab (MPDL3280), avelumab (MSB0010718C), durvalumab (MEDI-4736), and MDX-1105 (BMS-936559), or pharmaceutically acceptable salts thereof. In certain embodiments, the derivative or the fragment can be a molecule sharing a distinct structure (e.g., 70%-99% similarity) and similar biological activity in common with an antibody described herein. In certain embodiments, the derivative or the fragment comprises 70-75%, 75-80%, 80-85%, 85-90%, 95-97%, or 97-99% sequence (i.e., nucleic acid and amino acid) identity with a PD-L1 inhibitor described herein.

Methods of determining sequence identity are known in the art. The identity or homology may be the degree of identity between any given query sequence, for example, the percentage of nucleotide bases or amino acid residues in the antibody sequence that are identical with the residue of a corresponding sequence to which it is compared. Methods and computer programs for the alignment are available and well known in the art. See for example international publication numbers WO2007084385 and WO2012113863.

The variable region typically refers to a portion of an antibody, generally, a portion of a light or heavy chain (e.g., about the amino-terminal 110 to 120 amino acids in a mature heavy chain and about the amino-terminal 90 to 100 amino acids in a mature light chain) which is used in the binding and specificity of a particular antibody for its particular antigen. The variability in sequence is concentrated in those regions called complementarity determining regions while the more highly conserved regions in the variable domain are called framework regions (FR).

In certain embodiments the PD-L1 inhibitor of the invention comprises a heavy chain encoded by an amino acid sequence having at least 70%, 75%, 80%, 85%, 90%, 95%, or 99% identity with the amino acid sequence represented by SEQ ID NO.: 1. The present invention also relates to an PD-L1 inhibitor comprising a light chain having an amino acid sequence with at least 70%, 75%, 80%, 85%, 90%, 95%, or 99% identity with the amino acid sequence represented by SEQ ID NO.: 2. In various embodiments, the PD-L1 inhibitor comprises a heavy chain encoded by an amino acid sequence having at least 70%, 75%, 80%, 85%, 90%, 95%, or 99% identity with the amino acid sequence represented by SEQ ID NO.: 1; and comprises a light chain having an amino acid sequence with at least 70%, 75%, 80%, 85%, 90%, 95%, or 99% identity with the amino acid sequence represented by SEQ ID NO.: 2.

In certain embodiments, the variable domains of heavy and light chains each comprise complementarity determining regions (CDRs) which bind to PD-L1. See Kabat et al., 1987 Sequences of Proteins of Immunological Interest, National Institute of Health, Bethesda, Md., For the heavy chain variable region, the hypervariable region ranges from amino acid positions 31 to 35 for CDR1, amino acid positions 50 to 65 for CDR2, and amino acid positions 95 to 106 for CDR3. For the light chain variable region, the hypervariable region ranges from amino acid positions 24 to 34 for CDR1, amino acid positions 50 to 56 for CDR2, and amino acid positions 89 to 97 for CDR3. See for example U.S. Pat. No. 7,709,226 B2.

The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs can be referred to as Kabat CDRs. Chothia and coworkers (Chothia and Lesk (1987) J. Mol. Biol. 196:901-917) and Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-745. Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although particular embodiments use Kabat or Chothia defined CDRs. See for example international publication number WO2016149368.

In certain embodiments, the PD-L1 inhibitor includes the complementarity determining regions (CDR) sequences of an antibody described herein. For example, the PD-L1 inhibitor comprises a binding domain that comprises one or more CDR regions found within an antibody described herein, e.g., atezolizumab and avelumab. In certain embodiments, the PD-L1 inhibitor comprises at least one CDR found within the heavy chain amino acid sequence of SEQ ID NO.: 1. In certain embodiments, the PD-L1 inhibitor comprises one CDR, two CDRs or three CDRs found within the heavy chain amino acid sequence of SEQ ID NO.: 1. In certain embodiments, the PD-L1 inhibitor comprises one CDR, two CDRs or three CDRs found within the light chain amino acid sequence of SEQ ID NO.: 2. In various embodiments the PD-L1 inhibitor of the invention comprises at least one heavy chain CDR having at least 70%, 75%, 80%, 85%, 90%, 95%, or 99% identity with at least one CDRs found within the amino acid sequence of SEQ ID NO.: 1. In various embodiments, the PD-L1 inhibitor comprises a light chain CDR having at least 70%, 75%, 80%, 85%, 90%, 95%, or 99% identity with at least one CDR found within the amino acid sequence of SEQ ID NO.: 2.

Methods for Treating

Provided herein is a method for treating cancer in a subject in need thereof comprising administering to the subject a therapeutically effective amount of a pharmaceutical combination provided herein, i.e., a pharmaceutical combination comprising:

(a) a HDAC6 inhibitor of Formula I:

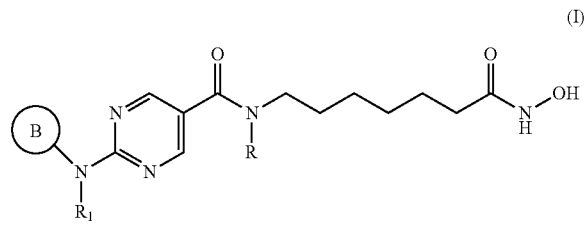

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl; and (b) a programmed death ligand 1 (PD-L1) inhibitor.

In an embodiment of the method, ring B is aryl. In various embodiments, $R_1$ is aryl or heteroaryl, substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by halo.

In yet another embodiment of Formula I, $R_1$ is phenyl that is substituted by chloro.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In another embodiment of the method, the HDAC6 inhibitor is Compound A, or a pharmaceutically acceptable salt thereof. In another embodiment of the method, the HDAC6 inhibitor is Compound B, or a pharmaceutically acceptable salt thereof.

In various embodiments of the methods, the PD-L1 inhibitor is an inhibitory antibody, e.g., selected from the group consisting of atezolizumab (MPDL3280), avelumab (MSB0010718C), MDX-1105 (BMS-936559), and durvalumab (MEDI-4736), or pharmaceutically acceptable salts thereof.

In an embodiment, provided herein is a method for treating cancer in a subject in need thereof comprising administering to the subject a therapeutically effective amount of a pharmaceutical combination provided herein.

The method provided herein can be used for both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In an embodiment of any of the method provided herein, the cancer is selected from a benign or malignant tumor of the lung (including small cell lung cancer and non-small-cell lung cancer), breast (including sporadic breast cancers and sufferers of Cowden disease), pancreas, gastrointestinal tract, colon, colon adenocarcinoma, liver, gastric carcinoma, mixed glioma, CNS (including glioblastoma), kidney, renal, bladder, ovary, head and neck, multiple myeloma, esophagus, a melanoma, a leukemia (including acute myelogenous leukemia (AML), chronic myelogenous leukemia (CML), acute lymphoblastic leukemia (ALL), chronic lymphoblastic leukemia (CLL), myelodysplastic syndromes, megakaryoblastic leukemia, erythroleukemia and myeloid leukemia), and a lymphoma (including non-Hodgkin lymphoma and Hodgkin's lymphoma).

In various embodiments, the cancer is a lymphoma, leukemia, or myeloma. In particular embodiments, the cancer is non-Hodgkin's lymphoma (NHL), chronic myelogenous leukemia (CML), acute myelogenous leukemia (AML), or multiple myeloma (MM). In further embodiments, the cancer is T-cell lymphoma or B-cell lymphoma.

In various embodiments of the pharmaceutical combination, the cancer is a non-solid tumor. In particular embodiments, the cancer is multiple myeloma.

In some embodiments, provided herein is a method for treating a cancer in a subject in need thereof, comprising administering to the subject a therapeutically effective amount of Compound A, or a pharmaceutically acceptable salt thereof, and a therapeutically effective amount of a PD-L1 inhibitor.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of a PD-L1 inhibitor, or a pharmaceutically acceptable salt thereof. In some embodiments, provided herein is a method for treating a hematological cancer in a subject in need thereof, comprising administering to the subject a therapeutically effective amount of Compound A, or a pharmaceutically acceptable salt thereof, and a therapeutically effective amount of a PD-L1 inhibitor, or a pharmaceutically acceptable salt thereof.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of a PD-L1 inhibitor, or a pharmaceutically acceptable salt thereof. In some embodiments, provided herein is a method for treating a leukemia in a subject in need thereof, comprising administering to the subject a therapeutically effective amount of Compound A, or a pharmaceutically acceptable salt thereof, and a therapeutically effective amount of a PD-L1 inhibitor, or a pharmaceutically acceptable salt thereof.

In another embodiment is a method for treating a cancer in a subject in need thereof, comprising administering to the subject a therapeutically effective amount of Compound A, or a pharmaceutically acceptable salt thereof, and a therapeutically effective amount of a PD-L1 antibody, or a pharmaceutically acceptable salt thereof. This embodiment exhibits synergy such that sub-therapeutic amounts of Compound A or of a PD-L1 antibody can be used in the method.

In another embodiment is a method for treating a hematological cancer in a subject in need thereof, comprising administering to the subject a therapeutically effective amount of Compound A, or a pharmaceutically acceptable salt thereof, and a therapeutically effective amount of a PD-L1 antibody, or a pharmaceutically acceptable salt thereof.

In another embodiment is a method for treating a leukemia in a subject in need thereof, comprising administering to the subject a therapeutically effective amount of Compound A, or a pharmaceutically acceptable salt thereof, and a therapeutically effective amount of a PD-L1 antibody, or a pharmaceutically acceptable salt thereof.

In yet another embodiment is a method for treating a cancer in a subject in need thereof, comprising administering to the subject a therapeutically effective amount of Compound A, or a pharmaceutically acceptable salt thereof, and a therapeutically effective amount of a PD-L1 inhibitor selected from the group consisting of atezolizumab (MPDL3280), avelumab (MSB0010718C), durvalumab (MEDI-4736), and MDX-1105 (BMS-936559), or pharmaceutically acceptable salts thereof.

In other embodiments, provided herein is a method for treating a cancer in a subject in need thereof, comprising administering to the subject a therapeutically effective amount of Compound B, or a pharmaceutically acceptable salt thereof, and a therapeutically effective amount of a PD-L1 inhibitor, or a pharmaceutically acceptable salt thereof.

In some embodiments, the method comprises administering to the subject a therapeutically effective amount of Compound B, or a pharmaceutically acceptable salt thereof, and a therapeutically effective amount of a PD-L1 inhibitor selected from the group consisting of atezolizumab (MPDL3280), avelumab (MSB0010718C), durvalumab (MEDI-4736), and MDX-1105 (BMS-936559), or pharmaceutically acceptable salts thereof.

In some embodiments, provided herein is a method for treating a hematological cancer in a subject in need thereof, comprising administering to the subject a therapeutically effective amount of Compound B, or a pharmaceutically acceptable salt thereof, and a therapeutically effective amount of a PD-L1 inhibitor, or a pharmaceutically acceptable salt thereof.

In some embodiments, provided herein is a method for treating a leukemia in a subject in need thereof, comprising administering to the subject a therapeutically effective amount of Compound B, or a pharmaceutically acceptable salt thereof, and a therapeutically effective amount of a PD-L1 inhibitor, or a pharmaceutically acceptable salt thereof.

In another embodiment is a method for treating a cancer in a subject in need thereof, comprising administering to the subject a therapeutically effective amount of Compound B, or a pharmaceutically acceptable salt thereof, and a therapeutically effective amount of a PD-L1 antibody, or a pharmaceutically acceptable salt thereof. This embodiment exhibits synergy such that sub-therapeutic amounts of Compound B or of a PD-L1 antibody can be used in the method.

In another embodiment is a method for treating a hematological cancer in a subject in need thereof, comprising administering to the subject a therapeutically effective amount of Compound B, or a pharmaceutically acceptable salt thereof, and a therapeutically effective amount of a PD-L1 antibody, or a pharmaceutically acceptable salt thereof.

In another embodiment is a method for treating a leukemia in a subject in need thereof, comprising administering to the subject a therapeutically effective amount of Compound B, or a pharmaceutically acceptable salt thereof, and a therapeutically effective amount of a PD-L1 antibody, or a pharmaceutically acceptable salt thereof.

The subject considered herein is typically a human. However, the subject can be any mammal for which treatment is desired. Thus, the methods described herein can be applied to both human and veterinary applications.

In a particular embodiment of the methods provided herein, the pharmaceutical combination comprises:
(a) Compound B:

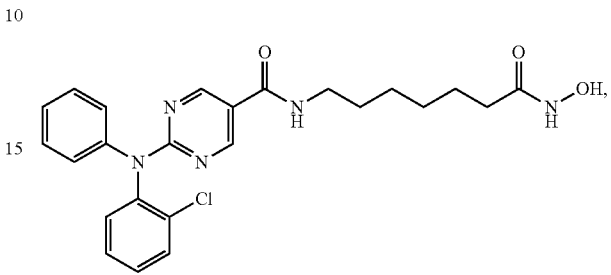

or a pharmaceutically acceptable salt thereof; and
(b) a PD-L1 inhibitor, or a pharmaceutically acceptable salt thereof. In an embodiment of this embodiment, the PD-L1 inhibitor is MDX-1105, or a pharmaceutically acceptable salt thereof. In yet a further embodiment of the methods provided herein, the pharmaceutical combination comprising Compound B, or a pharmaceutically acceptable salt thereof, and MDX-1105, or a pharmaceutically acceptable salt thereof, further comprises pomalidomide, or a pharmaceutically acceptable salt thereof.

In an aspect, provided herein is a method for upregulating antibody-dependent cell-mediated cytotoxicity in a subject in need thereof, comprising administering to the subject a therapeutically effective amount of any one of the pharmaceutical combinations provided herein.

In an aspect, provided herein is a method for upregulating lymphocyte functional activity in a subject in need thereof, comprising administering to the subject a therapeutically effective amount of any one of the pharmaceutical combinations provided herein.

In various embodiments, the lymphocyte is a natural killer cell. In other embodiments, the lymphocyte is a T lymphocyte. In other embodiments, the T lymphocyte is a cytotoxic T lymphocyte.

In various embodiments of the methods, the method further comprises administering to the subject a therapeutically effective amount of dexamethasone.

Pharmaceutical Combinations and Compositions

Provided herein is a pharmaceutical combination comprising a histone deacetylase inhibitor 6 (HDAC6) inhibitor and a PD-L1 inhibitor.

In an aspect, provided herein is a pharmaceutical combination comprising:
(a) a HDAC6 inhibitor of Formula I:

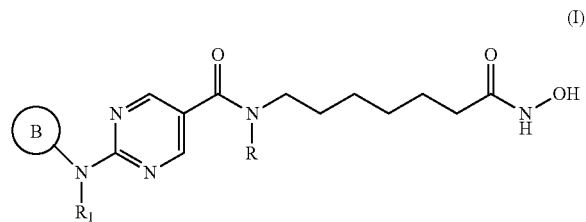

(I)

or a pharmaceutically acceptable salt thereof, wherein, ring B is aryl or heteroaryl $R_1$ is aryl or heteroaryl, each of which may be optionally substituted by OH, halo, or $C_{1-6}$-alkyl; and (b) a programmed death ligand 1 (PD-L1) inhibitor.

In various embodiments of the pharmaceutical combination, ring B is aryl.

In various embodiments of the pharmaceutical combination, the $R^1$ is aryl or heteroaryl, each of which is substituted by halo.

In various embodiments of the pharmaceutical combination, the compound of Formula I is Compound A, or a pharmaceutically acceptable salt thereof. In another embodiment, the compound of Formula I is Compound B, or a pharmaceutically acceptable salt thereof.

In various embodiments of the pharmaceutical combination, the PD-L1 inhibitor is an inhibitory antibody, such as atezolizumab, avelumab, MDX-1105, and durvalumab.

In various embodiments of the pharmaceutical combination, the HDAC6 inhibitor and the PD-L1 inhibitor are in the same formulation. Alternatively, the HDAC6 inhibitor and the PD-L1 inhibitor are in separate formulations.

In various embodiments, the pharmaceutical combination is for use in treating cancer in a subject in need thereof.

In an embodiment, the combination is used for the treatment of cancer comprising administering to the subject a combination therapy, comprising an effective amount of the HDAC6 inhibitor (i.e., compounds of Formula I such as Compound B) and an effective amount of a PD-L1 inhibitor. Preferably, these compounds are administered at therapeutically effective dosages which, when combined, provide a beneficial effect. The administration can comprise the separate administration of each component, either simultaneously, or sequentially.

In various embodiments, the pharmaceutical combination is for use in the preparation of a medicament for the treatment of cancer.

The pharmaceutical combination provided herein can also inhibit the growth of both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In an embodiment of any of the pharmaceutical combinations provided herein, the cancer is selected from a benign or malignant tumor of the lung (including small cell lung cancer and non-small-cell lung cancer), breast (including sporadic breast cancers and sufferers of Cowden disease), pancreas, gastrointestinal tract, colon, colon adenocarcinoma, liver, gastric carcinoma, mixed glioma, CNS (including glioblastoma), kidney, renal, bladder, ovary, head and neck, multiple myeloma, esophagus, a melanoma, a leukemia (including acute myelogenous leukemia (AML), chronic myelogenous leukemia (CML), acute lymphoblastic leukemia (ALL), chronic lymphoblastic leukemia (CLL), myelodysplastic syndromes, megakaryoblastic leukemia, erythroleukemia and myeloid leukemia), and a lymphoma (including non-Hodgkin lymphoma and Hodgkin's lymphoma).

In various embodiments, the cancer is a lymphoma, leukemia, or myeloma (i.e., a hematologic cancer). In particular embodiments, the cancer is non-Hodgkin's lymphoma (NHL), chronic myelogenous leukemia (CML), acute myelogenous leukemia (AML), or multiple myeloma (MM). In further embodiments, the cancer is a T-cell lymphoma or a B-cell lymphoma.

In various embodiments of the pharmaceutical combination, the cancer is a non-solid cancer. In particular embodiments, the cancer is multiple myeloma.

In various embodiments, the cancer is resistant or refractory to treatment with at least one prior therapy.

In a particular embodiment, the pharmaceutical combination comprises:

(a) Compound B:

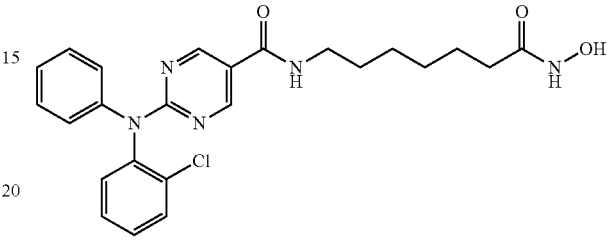

or a pharmaceutically acceptable salt thereof; and (b) a PD-L1 inhibitor, or a pharmaceutically acceptable salt thereof. In an embodiment of this embodiment, the PD-L1 inhibitor is MDX-1105, or a pharmaceutically acceptable salt thereof. In yet a further embodiment of the combination comprising Compound B, or a pharmaceutically acceptable salt thereof, and MDX-1105, or a pharmaceutically acceptable salt thereof, the combination further comprises pomalidomide, or a pharmaceutically acceptable salt thereof.

Data provided herein shows that a combination therapy comprising a HDAC6 inhibitor of Formula I and a PD-L1 inhibitor increases antibody-dependent cell-mediated cytotoxicity and apoptosis to a more significant extent relative to either single agent alone (see, e.g., Example 5 and Example 6).

Compounds of Formula I, or the PD-L1 inhibitor, can be administered in free form or in a pharmaceutically acceptable salt form.

In various embodiments of the pharmaceutical combinations, the combination further comprises dexamethasone.

Provided herein are pharmaceutical compositions comprising a histone deacetylase inhibitor (HDAC) inhibitor and a PD-L1 inhibitor.

As used herein, term "pharmaceutical composition" is defined herein to refer to a mixture or solution containing the therapeutic agent(s) to be administered to a subject, e.g., a mammal or human, in order to prevent or treat a particular disease or condition affecting the mammal.

In an aspect, provided herein is a pharmaceutical composition comprising (a) a HDAC6 inhibitor of Formula I:

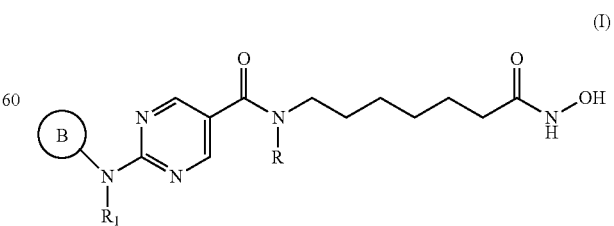

or a pharmaceutically acceptable salt thereof, wherein, ring B is aryl or heteroaryl;

$R_1$ is aryl or heteroaryl, each of which may be optionally substituted by OH, halo, or $C_{1-6}$-alkyl; and R is H or $C_{1-6}$-alkyl; and (b) a programmed death ligand 1 (PD-L1) inhibitor.

In an embodiment of the composition, ring B is aryl. In various embodiments, $R_1$ is aryl or heteroaryl, which is substituted by halo.

In another embodiment of the composition, the HDAC6 inhibitor is Compound A, or a pharmaceutically acceptable salt thereof. In another embodiment of the composition, the HDAC6 inhibitor is Compound B, or a pharmaceutically acceptable salt thereof.

In various embodiments of pharmaceutical composition, the PD-L1 inhibitor is an inhibitory antibody, e.g., selected from the group consisting of atezolizumab (MPDL3280), avelumab (MSB0010718C), MDX-1105 (BMS-936559), or durvalumab (MEDI-4736), or pharmaceutically acceptable salts thereof.

In an embodiment of the composition, the pharmaceutical composition further comprises one or more excipients, e.g., a pharmaceutically acceptable excipient. As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

Unless otherwise specified, or clearly indicated by the text, reference to therapeutic agents useful in the pharmaceutical combination provided herein includes both the free base of the compounds, and all pharmaceutically acceptable salts of the compounds.

Administration/Dose

The method of treating cancer according to the disclosure provided herein can comprise (i) administration of the HDAC6 inhibitor (a) in free or pharmaceutically acceptable salt form and (ii) administration of a PD-L1 inhibitor (b) in free or pharmaceutically acceptable salt form simultaneously or sequentially, in any order, in jointly therapeutically effective amounts, preferably in synergistically effective amounts, e.g., in daily or intermittent dosages. The individual combination partners of the pharmaceutical combination provided herein can be administered separately at different times during the course of therapy or concurrently in divided or single combination forms. The method provided herein is therefore to be understood as embracing all such regimens of simultaneous or alternating treatment and the term "administering" is to be interpreted accordingly. For example, in one embodiment of the method, the HDAC6 inhibitor is administered first, followed by the PD-L1 inhibitor. In another embodiment of the method, the PD-L1 inhibitor is administered first, followed by the HDAC6 inhibitor.

Compounds of Formula I can be orally administered in an amount from about 10 mg to about 1000 mg (including e.g., about 10 mg to about 500 mg) per day in single or multiple doses. Thus, in an embodiment of the methods of treatment provided herein, the compound of Formula I is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the compound of Formula I is administered at a dosage of 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 180 mg, or 200 mg per day.

In an embodiment of the pharmaceutical combination, Compound A is in an amount from 600 mg to 3000 mg (e.g., about 600, about 800, about 1000, about 1200, about 1400, about 1600, about 1800, about 2000 mg). In a further embodiment of the pharmaceutical combination, Compound A is in an amount from 600 mg to 2000 mg. In a preferred embodiment of the pharmaceutical combination, Compound A is in an amount from 180 mg to 480 mg.

In another embodiment of the pharmaceutical combination, Compound A is in an amount from 5 mg to 600 mg (e.g., about 5, about 25, about 50, about 100, about 200, about 300, about 400, about 500, about 600 mg). In yet another embodiment of the pharmaceutical combination Compound A is 10 mg to 200 mg.

In an embodiment of the pharmaceutical combination, Compound B is in an amount from 600 mg to 3000 mg (e.g., about 600, about 800, about 1000, about 1200, about 1400, about 1600, about 1800, about 2000 mg). In a further embodiment of the pharmaceutical combination, Compound B is in an amount from 600 mg to 2000 mg. In a preferred embodiment of the pharmaceutical combination, Compound B is in an amount from 180 mg to 480 mg.

In another embodiment of the pharmaceutical combination, Compound B is in an amount from 5 mg to 600 mg (e.g., about 5, about 25, about 50, about 100, about 200, about 300, about 400, about 500, about 600 mg). In yet another embodiment of the pharmaceutical combination Compound B is 10 mg to 200 mg.

In an embodiment of the pharmaceutical combination, the PD-L1 inhibitor is in an amount from 600 mg to 3000 mg (e.g., about 600, about 800, about 1000, about 1200, about 1400, about 1600, about 1800, about 2000 mg). In a further embodiment of the pharmaceutical combination, the PD-L1 inhibitor is in an amount from 600 mg to 2000 mg.

In another embodiment of the pharmaceutical combination, the PD-L1 inhibitor is in an amount from 5 mg to 600 mg (e.g., about 5, about 25, about 50, about 100, about 200, about 300, about 400, about 500, about 600 mg). In yet another embodiment of the pharmaceutical combination, the PD-L1 inhibitor is 10 mg to 200 mg. In an embodiment of the pharmaceutical combination, the PD-L1 antibody is in an amount from 600 mg to 3000 mg (e.g., about 600, about 800, about 1000, about 1200, about 1400, about 1600, about 1800, about 2000 mg). In a further embodiment of the pharmaceutical combination, the PD-L1 antibody is in an amount from 600 mg to 2000 mg.

In another embodiment of the pharmaceutical combination, the PD-L1 antibody is in an amount from 5 mg to 600 mg (e.g., about 5, about 25, about 50, about 100, about 200, about 300, about 400, about 500, about 600 mg). In yet another embodiment of the pharmaceutical combination, the PD-L1 antibody is 10 mg to 200 mg.

The effective dosage of each of the combination partners employed in the combination of the invention may vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient.

The optimum ratios, individual and combined dosages, and concentrations of the combination partners (e.g., a compound of Formula I and the PD-L1 inhibitor) of the combination provided herein that yield efficacy without toxicity are based on the kinetics of the therapeutic agents' availability to target sites, and are determined using methods known to those of skill in the art.

In an embodiment of the pharmaceutical combination, the ratio of the compound of Formula I to the PD-L1 inhibitor is in the range of 700:1-1:40. In another embodiment, the ratio of the compound of Formula I to the PD-L1 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound A to the PD-L1 inhibitor is in the range of 700:1-1:40. In another embodiment, the ratio of Compound A to the PD-L1 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound B to the PD-L1 inhibitor is in the range of 700:1-1:40. In another embodiment, the ratio of Compound B to the PD-L1 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to the PD-L1 antibody is in the range of 700:1-1:40. In another embodiment, the ratio of Compound A to the PD-L1 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound B to the PD-L1 antibody is in the range of 700:1-1:40. In another embodiment, the ratio of Compound B to the PD-L1 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combinations of compounds, but not the other compound(s) of the combination.

When the combination partners, which are employed in the combination of the invention, are applied in the form as marketed as single drugs, their dosage and mode of administration can be in accordance with the information provided on the package insert of the respective marketed drug, if not mentioned herein otherwise.

The optimal dosage of each combination partner for treatment of a cancer can be determined empirically for each individual using known methods and will depend upon a variety of factors, including, though not limited to: the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone. Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

Also provided herein is a commercial package comprising, as therapeutic agents, the pharmaceutical combination provided herein, together with instructions for simultaneous, separate or sequential administration thereof for use in the delay of progression or treatment of a cancer.

It can be shown by established test models that a pharmaceutical combination as provided herein results in the beneficial effects described herein before. The person skilled in the art is fully enabled to select a relevant test model to prove such beneficial effects. The pharmacological activity of the pharmaceutical combinations provided herein may, for example, be demonstrated in a clinical study or in an animal model.

In an embodiment, the pharmaceutical combination or composition, or both, provided herein display a synergistic effect. In another embodiment, the pharmaceutical combination or composition is administered at dosages that would not be effective when one or both of the HDAC inhibitor and the PD-L1 inhibitor is administered alone, but which amounts are effective in combination.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments can be predictive of the effect in other species, and animal models exist may be used to further quantify a synergistic effect. The results of such studies can also be used to predict effective dose ratio ranges and the absolute doses and plasma concentrations.

In a further embodiment, provided herein is a synergistic combination for administration to a subject comprising the combination of the invention, where the dose range of each component corresponds to the synergistic ranges suggested in a suitable tumor model or clinical study.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EXAMPLES

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1: Synthesis of 2-(diphenylamino)-N-(7-(hydroxyamino)-7-oxoheptyl)pyrimidine-5-carboxamide (Compound A) and 2-((2-chlorophenyl)(phenyl)amino)-N-(7-(hydroxyamino)-7-oxoheptyl)pyrimidine-5-carboxamide (Compound B)

I. Synthesis of 2-(diphenylamino)-N-(7-(hydroxyamino)-7-oxoheptyl)pyrimidine-5-carboxamide (Compound A)

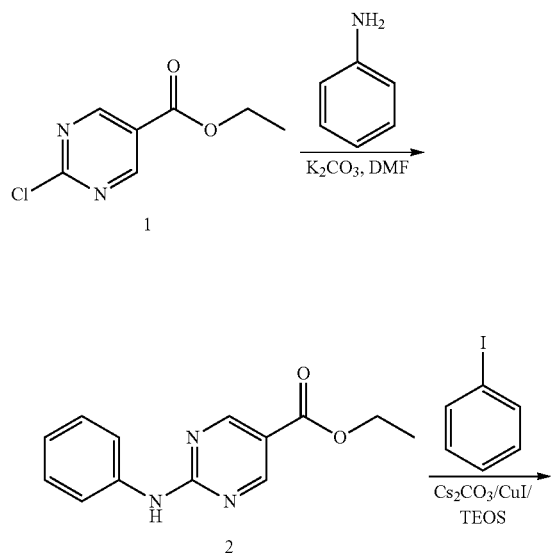

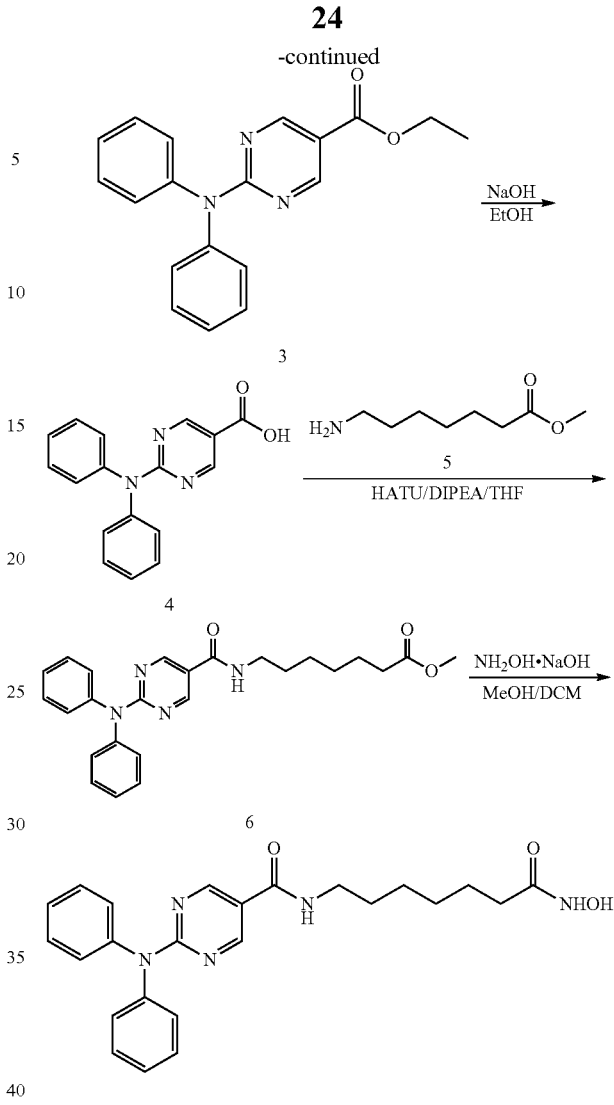

Synthesis of Intermediate 2: A mixture of aniline (3.7 g, 40 mmol), compound 1 (7.5 g, 40 mmol), and K$_2$CO$_3$ (11 g, 80 mmol) in DMF (100 ml) was degassed and stirred at 120° C. under N$_2$ overnight. The reaction mixture was cooled to r.t. and diluted with EtOAc (200 ml), then washed with saturated brine (200 ml×3). The organic layers were separated and dried over Na$_2$SO$_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), Cs$_2$CO$_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and NH$_4$F—H$_2$O on silica gel [50 g, pre-prepared by the addition of NH$_4$F (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na₂SO₄. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5 -carboxamide: A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-H PLC to give a white solid (950 mg, 48%).

II. Synthetic Route 1: 2-(((2-chlorophenyl)(phenyl)amino)-N-(7-(hydroxyamino)-7-oxoheptyl)pyrimidine-5-carboxamide (Compound B)

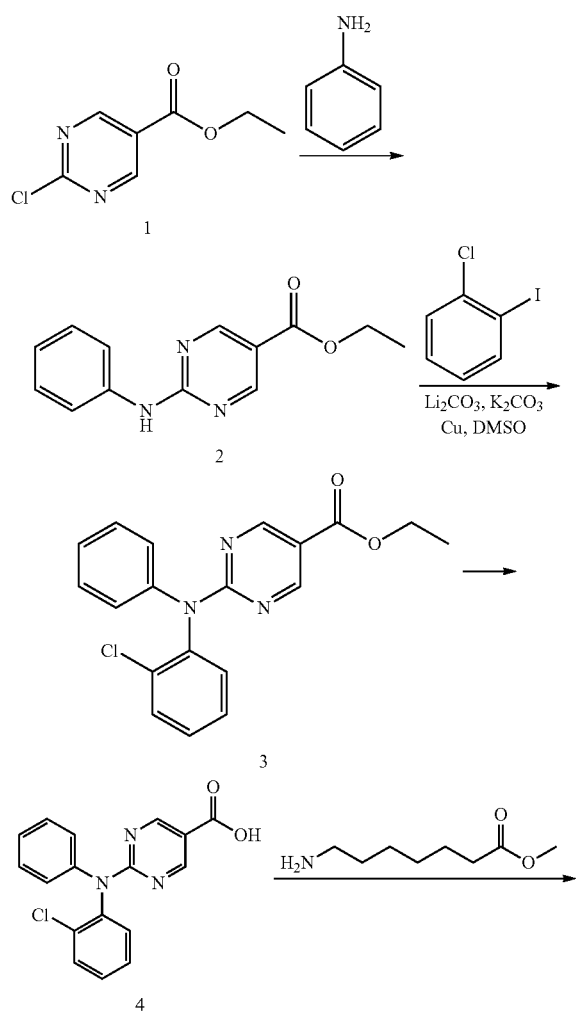

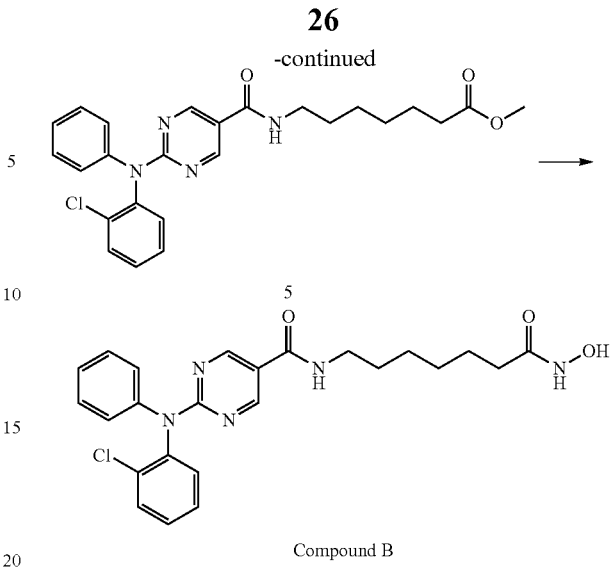

Compound B

Synthesis of Intermediate 2: A mixture of aniline (3.7 g, 40 mmol), ethyl 2-chloropyrimidine-5-carboxylate 1 (7.5 g, 40 mmol), K₂CO₃ (11 g, 80 mmol) in DMF (100 ml) was degassed and stirred at 120° C. under N₂ overnight. The reaction mixture was cooled to rt and diluted with EtOAc (200 ml), then washed with saturated brine (200 ml×3). The organic layer was separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3: A mixture of compound 2 (69.2 g, 1 equiv.), 1-chloro-2-iodobenzene (135.7 g, 2 equiv.), Li₂CO₃ (42.04 g, 2 equiv.), K₂CO₃ (39.32 g, 1 equiv.), Cu (1 equiv. 45 μm) in DMSO (690 ml) was degassed and purged with nitrogen. The resulting mixture was stirred at 140° C. for 36 hours. Work-up of the reaction gave compound 3 at 93% yield.

Synthesis of Intermediate 4: 2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over Na₂SO₄. Removal of solvent gave a brown solid (2.5 g, 92%).

Synthesis of Intermediate 5: A procedure analogous to the Synthesis of Intermediate 6 in Part I of this Example was used.

Synthesis of 2-((2-chlorophenyl)(phenyl)amino)-N-(7-(hydroxyamino)-7-oxoheptyl)pyrimidine-5-carboxamide: A procedure analogous to the Synthesis of 2-(diphenylamino)-N-(7-(hydroxyamino)-7-oxoheptyl)pyrimidine-5-carboxamide in Part I of this Example was used.

III. Synthetic Route 2: 2-((2-chlorophenyl)(phenyl)amino)-N-(7-(hydroxyamino)-7-oxoheptyl)pyrimidine-5-carboxamide (Compound B)

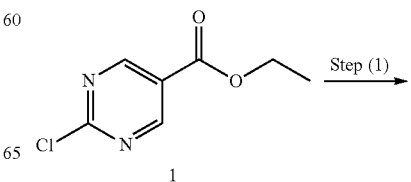

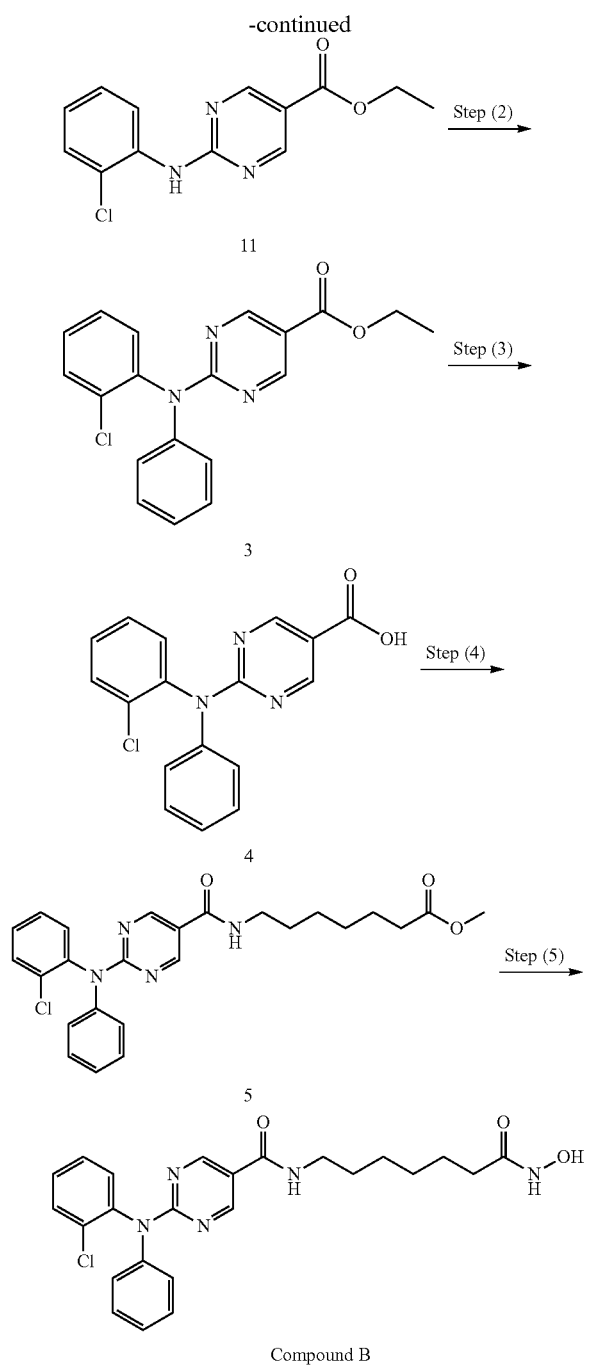

Step (1): Synthesis of Compound 11: Ethyl 2-chloropyrimidine-5-carboxylate (7.0 Kgs), ethanol (60 Kgs), 2-Chloroaniline (9.5 Kgs, 2 eq) and acetic acid (3.7 Kgs, 1.6 eq) were charged to a reactor under inert atmosphere. The mixture was heated to reflux. After at least 5 hours the reaction was sampled for HPLC analysis. When analysis indicated reaction completion, the mixture was cooled to 70±5° C. and N,N-Diisopropylethylamine (DIPEA) was added. The reaction was then cooled to 20±5° C. and the mixture was stirred for an additional 2-6 hours. The resulting precipitate is filtered and washed with ethanol (2×6 Kgs) and heptane (24 Kgs). The cake is dried under reduced pressure at 50±5° C. to a constant weight to produce 8.4 Kgs compound 11 (81% yield and 99.9% purity.

Step (2): Synthesis of Compound 3: Copper powder (0.68 Kgs, 1 eq, <75 micron), potassium carbonate (4.3 Kgs, 1.7 eq), and dimethyl sulfoxide (DMSO, 12.3 Kgs) were added to a reactor (vessel A). The resulting solution was heated to 120±5° C. In a separate reactor (vessel B), a solution of compound 11 (2.9 Kgs) and iodobenzene (4.3 Kgs, 2 eq) in DMSO (5.6 Kgs) was heated at 40±5° C. The mixture was then transferred to vessel A over 2-3 hours. The reaction mixture was heated at 120±5° C. for 8-24 hours, until HPLC analysis determined that ≤1% compound 11 was remaining.

Step (3): Synthesis of Compound 4: The mixture of Step (2) was cooled to 90-100° C. and purified water (59 Kgs) was added. The reaction mixture was stirred at 90-100° C. for 2-8 hours until HPLC showed that ≤1% compound 3 was remaining. The reactor was cooled to 25° C. The reaction mixture was filtered through Celite, then a 0.2 micron filter, and the filtrate was collected. The filtrate was extracted with methyl t-butyl ether twice (2×12.8 Kgs). The aqueous layer was cooled to 0-5° C., then acidified with 6N hydrochloric acid (HCl) to pH 2-3 while keeping the temperature <25° C. The reaction was then cooled to 5-15° C. The precipitate was filtered and washed with cold water. The cake was dried at 45-55° C. under reduced pressure to constant weight to obtain 2.2 kg (65% yield) compound 4 in 90.3% AUC purity.

Step (4): Synthesis of Compound 5: Dichloromethane (40.3 Kgs), DMF (33 g, 0.04 eq) and compound 4 (2.3 Kg) were charged to a reaction flask. The solution was filtered through a 0.2 μm filter and was returned to the flask. Oxalyl chloride (0.9 Kgs, 1 eq) was added via addition funnel over 30-120 minutes at <30° C. The batch was then stirred at <30° C. until reaction completion (compound 4≤3%) was confirmed by HPLC. Next, the dichloromethane solution was concentrated and residual oxalyl chloride was removed under reduced pressure at <40° C. When HPLC analysis indicated that <0.10% oxalyl chloride was remaining, the concentrate was dissolved in fresh dichloromethane (24 Kgs) and transferred back to the reaction vessel (Vessel A).

A second vessel (Vessel B) was charged with Methyl 7-aminoheptanoate hydrochloride (Compound A1, 1.5 Kgs, 1.09 eq), DIPEA (2.5 Kgs, 2.7 eq), 4 (Dimethylamino) pyridine (DMAP, 42 g, 0.05 eq), and DCM (47.6 Kgs). The mixture was cooled to 0-10° C. and the acid chloride solution in Vessel A was transferred to Vessel B while maintaining the temperature at 5° C. to 10° C. The reaction is stirred at 5-10° C. for 3 to 24 hours at which point HPLC analysis indicated reaction completion (compound 4≤5%). The mixture was then extracted with a 1M HCl solution (20 Kgs), purified water (20 Kgs), 7% sodium bicarbonate (20 Kgs), purified water (20 Kgs), and 25% sodium chloride solution (20 Kgs). The dichloromethane was then vacuum distilled at <40° C. and chased repeatedly with isopropyl alcohol. When analysis indicated that <1 mol % DCM was remaining, the mixture was gradually cooled to 0-5° C. and was stirred at 0-5° C. for an at least 2 hours. The resulting precipitate was collected by filtration and washed with cold isopropyl alcohol (6.4 Kgs). The cake was sucked dry on the filter for 4-24 hours, then was further dried at 45-55° C. under reduced pressure to constant weight. 2.2 Kgs (77% yield) was isolated in 95.9% AUC purity method and 99.9 wt %.

Step (5): Synthesis of Compound (I) Hydroxylamine hydrochloride (3.3 Kgs, 10 eq) and methanol (9.6 Kgs) were charged to a reactor. The resulting solution was cooled to 0-5° C. and 25% sodium methoxide (11.2 Kgs, 11 eq) was charged slowly, maintaining the temperature at 0-10° C. Once the addition was complete, the reaction was mixed at 20° C. for 1-3 hours and filtered, and the filter cake was washed with methanol (2×2.1 Kgs). The filtrate (hydroxylamine free base) was returned to the reactor and cooled to 0±5° C. Compound 5 (2.2 Kgs) was added. The reaction was stirred until the reaction was complete (compound 5≤2%). The mixture was filtered and water (28 Kgs) and ethyl acetate (8.9 Kgs) were added to the filtrate. The pH was adjusted to 8-9 using 6N HCl then stirred for up to 3 hours before filtering. The filter cake was washed with cold water (25.7 Kgs), then dried under reduced pressure to constant weight. The crude solid compound (I) was determined to be Form IV/Pattern D.

The crude solid (1.87 Kgs) was suspended in isopropyl alcohol (IPA, 27.1 Kg). The slurry was heated to 75±5° C. to dissolve the solids. The solution was seeded with crystals of Compound (I) (Form I/Pattern A), and was allowed to cool to ambient temperature. The resulting precipitate was stirred for 1-2 hours before filtering. The filter cake was rinsed with IPA (2×9.5 Kgs), then dried at 45-55° C. to constant weight under reduced pressure to result in 1.86 kg crystalline white solid Compound (I) in 85% yield and 99.5% purity (AUC %, e.g., by the HPLC method of Table 3).

TABLE 3

HPLC Method

| | |
|---|---|
| Column | Zorbax Eclipse XDB-018, 4.6 mm × 150 mm, 3.5 μm |
| Column Temperature | 40° C. |
| UV Detection Wavelength | Bandwidth 4 nm, Reference off, 272 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

Example 2: HDAC Enzyme Assay

Compound B was tested first by diluting the compound in DMSO to 50 fold the final concentration and a ten point three fold dilution series was made. The compound was diluted in assay buffer (50 mM HEPES, pH 7.4, 100 mM KCl, 0.001% Tween-20, 0.05% BSA, 20 μM TCEP) to 6 fold their final concentration. The HDAC enzymes (purchased from BPS Biosciences; San Diego, Calif.) were diluted to 1.5 fold their final concentration in assay buffer. The tripeptide substrate and trypsin at 0.05 μM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6). Five μl of compound and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. See Table 1 for $IC_{50}$ associated with Compounds A and B.

Example 3: Methods

Cell Lines

MM.1S, NCI-H929, RPMI8226 and U266 cell lines were obtained from American Type Culture Collection (Manassas, Va.). KMS11 and KMS12-PE cell lines were obtained from JCRB Cell Bank (Japan). The OPM-1 cell line (which is commercially available) was in this example provided by Dr. Leif Bergsagel (Mayo Clinic, AZ). All MM cell lines were cultured in RPMI-1640 containing 10% fetal bovine serum (FBS, Sigma Chemical Co., St. Louis, Mo.), 2 μM L-glutamine, 100 U/ml penicillin, and 100 μg/ml streptomycin (GIBCO, Grand Island, N.Y.).

Bone Marrow Stromal Cells (BMSCs)

Mononuclear cells separated by Ficoll-Hypaque density sedimentation from bone marrow aspirates were cultured in 15% FBS-RPMI1640 for 5-6 weeks to establish long-term bone marrow stromal cells. Culture supernatant from BMSCs was used for stimulation of MM cell lines.

Reagents

Compound A and Compound B were provided by Acetylon Pharmaceuticals. Anti-PD-L1 antibodies were provided by Acetylon Pharmaceuticals.

Antibody-Dependent Cell-Mediated (ADCC) Assay Using MM Cell Lines In Vitro

Multiple myeloma cells were incubated with Calcein-AM (Invitrogen, 2 μg/ml/1 million cells) for 30 min at 37° C. After washing, the cells were used for target cells. Mononuclear cells were obtained from healthy volunteer peripheral blood by Ficoll-Paque density centrifugation and used for effector cells. Both target and effector cells (E/T=15-20) were incubated for 3-4 h and culture supernatant were subjected to measurement of fluorescence using a 490 nm excitation filter and a 520 emission filter. Percent specific lysis was calculated as follows, % specific lysis=[experiment fluorescence−spontaneous fluorescence (no effector)]/[complete lysis (100% killing by detergent)−spontaneous fluorescence (no effector)]×100.

Flow Cytometry-Based Ex Vivo ADCC Assay

After bone marrow aspiration, fresh bone marrow mononuclear cells (MNC) were obtained by ammonium chloride based-lyses of red cells followed by washing in phosphate-buffered saline (PBS). For ADCC assays, cells were immediately incubated with anti-PD-L1 antibody (BMS-936559, also referred to herein as "MDX-1105" 1 μg/mL) in the presence of Compound A or Compound B in complete medium in 96-well plate. The cells were incubated for 72 h at 37° C. in a 5% $CO_2$ environment. The viability of primary MM cells in BM MNC was determined by near infrared (n-IR) viability dyes. The surviving CD138+ MM cells were enumerated in the presence of Flow-Count Fluorospheres (Beckman Coulter, CA, USA), to determine absolute numbers of viable MM cells. Phenotypic analyses of MNC were performed using a single 5-color combination of monoclonal antibodies containing BV421/PD-L1(CD274)-BV711 (BD Biosciences, San Jose, Calif., USA). PD-L1 on plasma cells was determined using a commercial assay (BD Biosciences, San Jose, Calif., USA). After incubation, cells were washed twice in PBS containing 2% BSA, and then re-suspended in PBS for analysis on a Fortessa cytometer (Becton Dickinson, Mountain View, Calif.). MM cell lines were also applied to this method in some experiments.

RNA Extraction and Reverse Transcription Polymerase Chain Reaction

RNA was extracted using Trizol (Invitrogen) and quantified by a Nanodrop spectrophotometer (Labtech). Specifically, an amount ($5 \times 10^6$) cells were pelleted, washed with cold PBS, and re-suspended in 1 mL of Trizol. The re-suspended cells were then incubated with 1-Bromo-3-chloropropane (Sigma), washed first with isopropyl alcohol and then with 75% ethanol, and re-suspended in Nuclease Free-water (Invitrogen). After quantification, 2000 ng of RNA was used to synthesize cDNA using the Superscript II First strand synthesis Kit (Invitrogen), according to the manufacturer's instructions. Primer information of PD-L1 for real-time qPCR is, forward: TGACCAGCACACTGAGAATCAA; reverse: TGGAGGATGTGCCAGAGGT.

Example 4: PD-L1 Expression is Enhanced by HDAC6 Inhibitors

To assess the effect of HDAC6 inhibitors on the expression of PD-L1, H929 multiple myeloma cells were cultured with lenalidomilde (LEN, 1 µM and 3 µM), pomalidomide (POM, 1 µM), or Compound A (1 µM and 2 µM) for 48 hours. Data show that PD-L1 expression increased in cells treated with HDAC6 inhibitor as assessed by flow cytometry (FCM) (FIG. 1).

Figure 2:
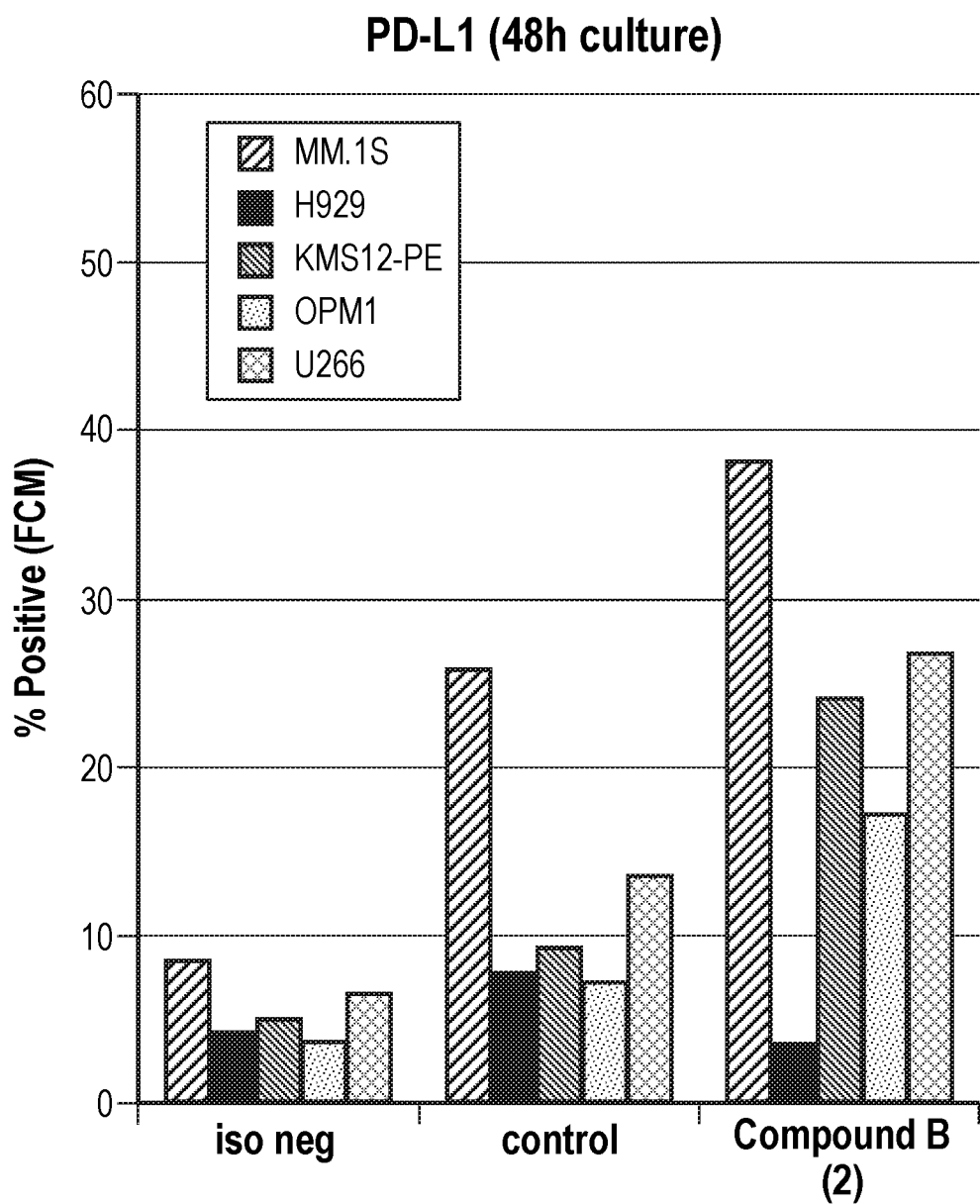
FIG. 2 is a bar graph showing the expression of PD-L1 in MM.1S, H929, KMS12-PE, OPM1, and U266 myeloma cells cultured for 48 hours with Compound B.

Similarly, when MM.1S, H929, KMS12-PE, OPM1 and U266 multiple myeloma cells were cultured with Compound B (2 µM) for 48 hours, data show that PD-L1 expression was enhanced in cells cultured with inhibitor (FIG. 2).

Figure 3:
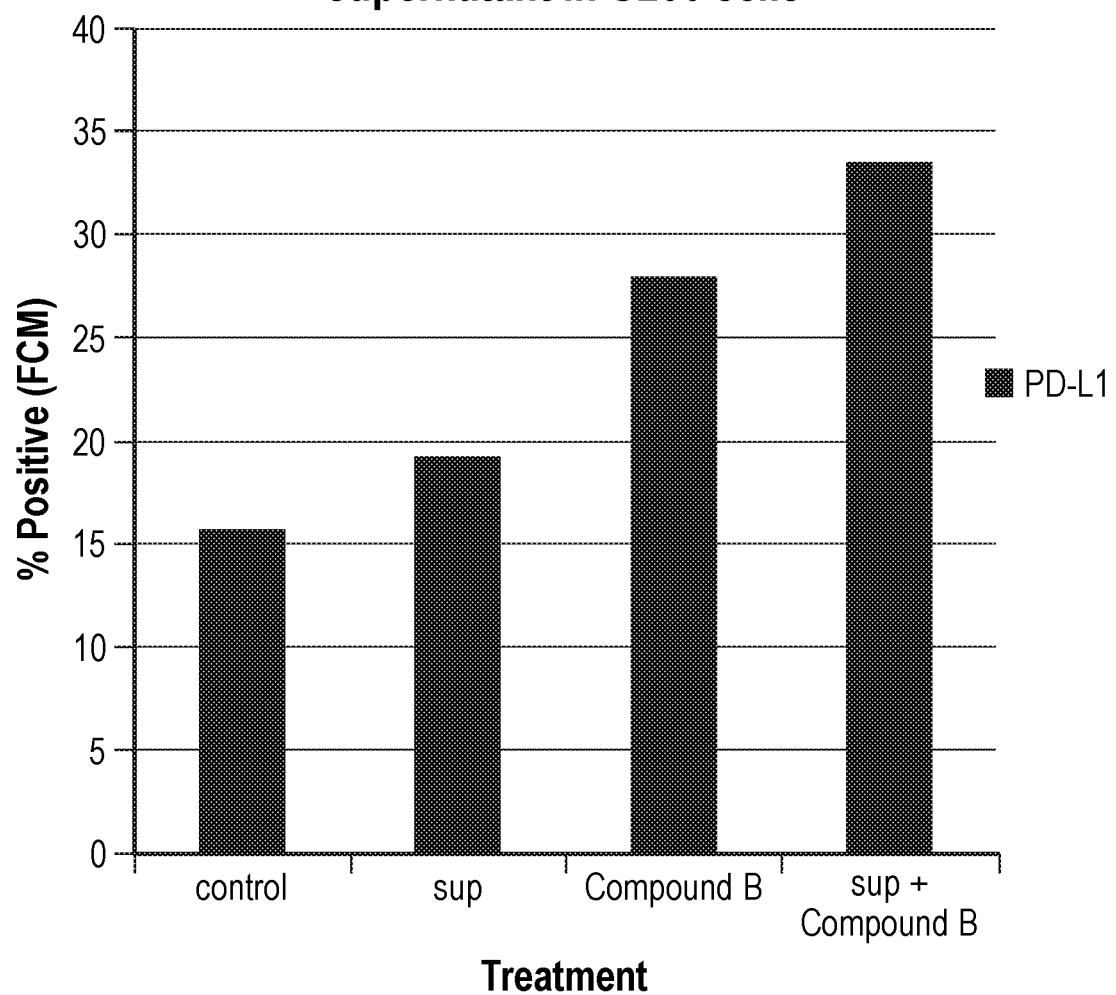
FIG. 3 is a bar graph showing PD-L1 expression in U266 cells cultured in stromal cell supernatant in the presence or absence of Compound B.

To determine the effect stromal cell priming has on PD-L1 expression in U266 cells treated with Compound B, U266 cells were cultured in stromal cell supernatant (sup) in the presence or absence of Compound B (1 µM) for 48 hours. PD-L1 expression was assessed by FCM. Expression of PD-L1 was highest in cells cultured in stromal cell supernatant in the presence of Compound B (FIG. 3).

Figure 4:
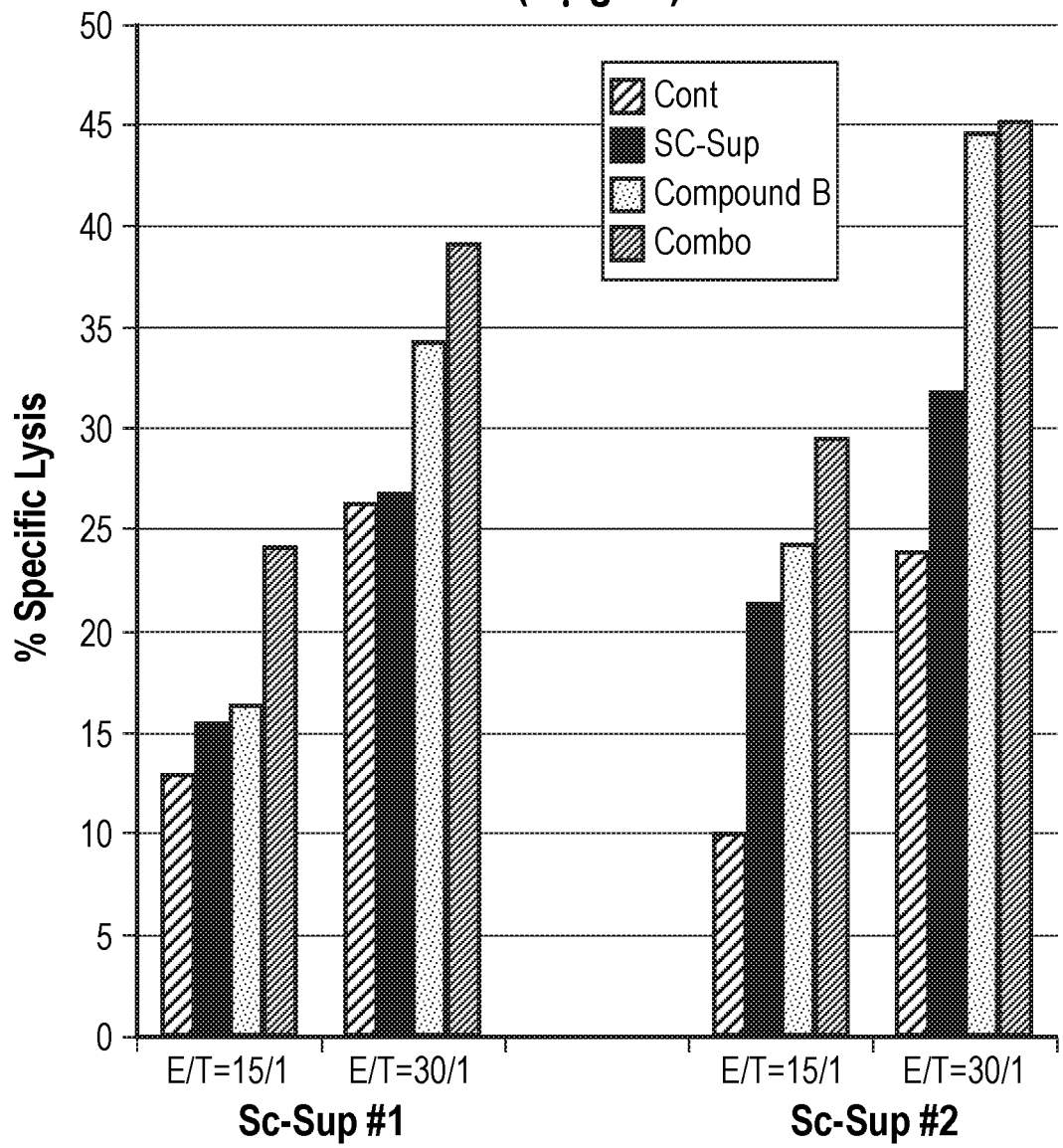
FIG. 4 is a bar graph showing the effect of Compound B plus stromal cell supernatant on anti-PD-L1 antibody-dependent cell-mediated cytotoxicity in U266 cells.

Example 5: Anti-PD-L1 Antibody-Dependent Cell-Mediated Cytotoxicity is Enhanced by Stromal Cell Supernatant, Pomalidomide, and Compound B To assess the effect of the combination of Compound B and stromal cell supernatant on anti-PD-L1 antibody-dependent cell mediated cytotoxicity, U266 cells were cultured with Compound B (1 µM) and/or stromal cell supernatant from two separate sources for 48 hours. The cells were then incubated with anti-PD-L1 antibody (1 µg/ml) and peripheral blood mononuclear cells (E/T=15/1 and 30/1) for 5 hours. In both groups, the greatest percent specific lysis was observed in cells cultured with both Compound B and stromal cell supernatant as assessed by FCM (FIG. 4).

Figure 5:
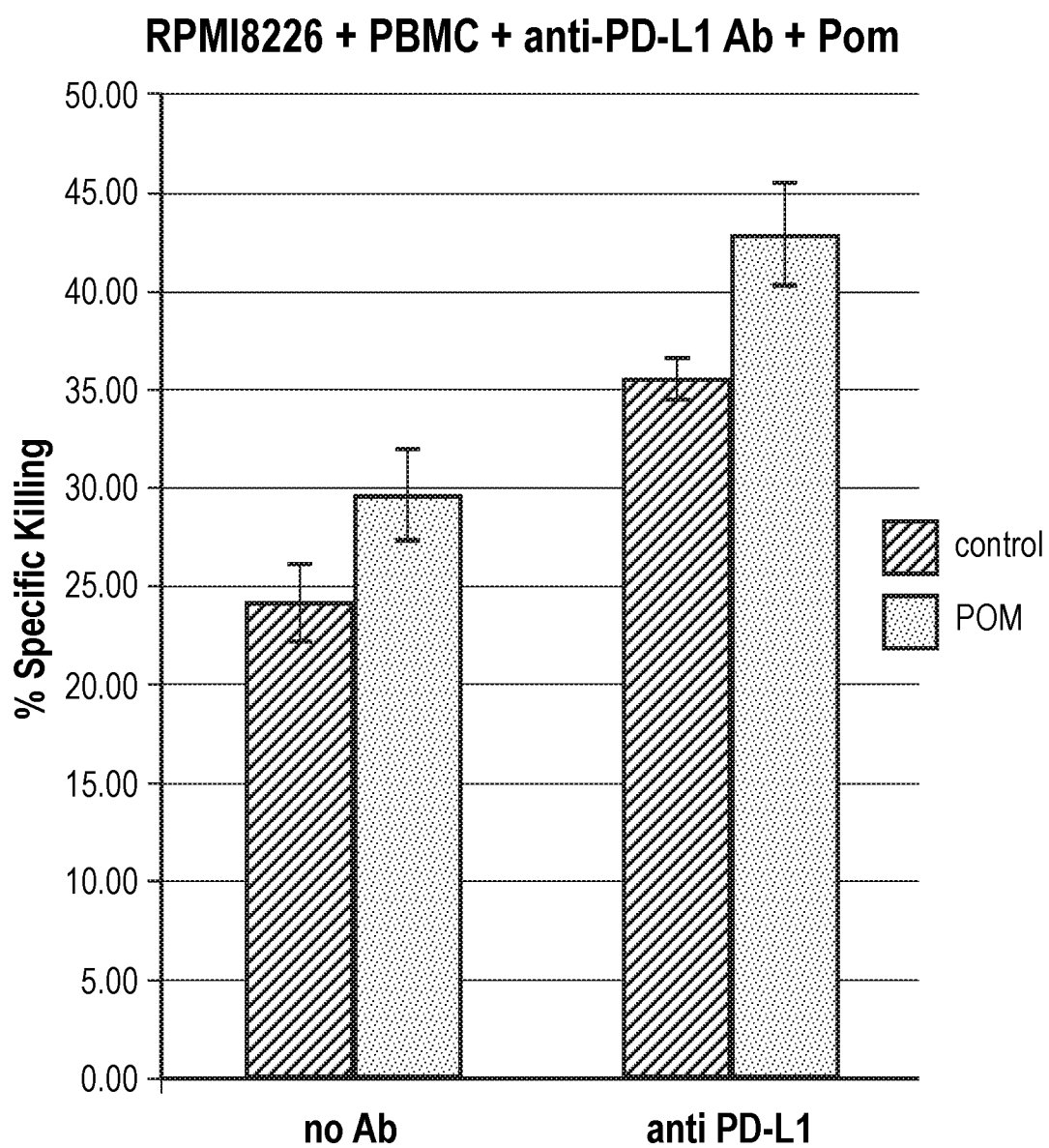
FIG. 5 is a bar graph showing the effect of pomalidomide on anti-PD-L1 antibody-dependent cell-mediated cytotoxicity in RPMI8266 cells.

Similarly, RPMI8226 cells were cultured with PBMCs (E/T=15/1) in the presence or absence of pomalidomide (Pom, 0.1 µM) for 72 hours. After subsequent cultivation with anti-PD-L1 antibody (0.5 µg/ml) for 3 hours, percent specific killing was assessed by FCM. Pomalidomide treatment of cells enhanced cytotoxicity (FIG. 5).

Example 6: Compound B Enhances Antibody-Dependent Cell-Mediated Cytotoxicity

Figure 6:
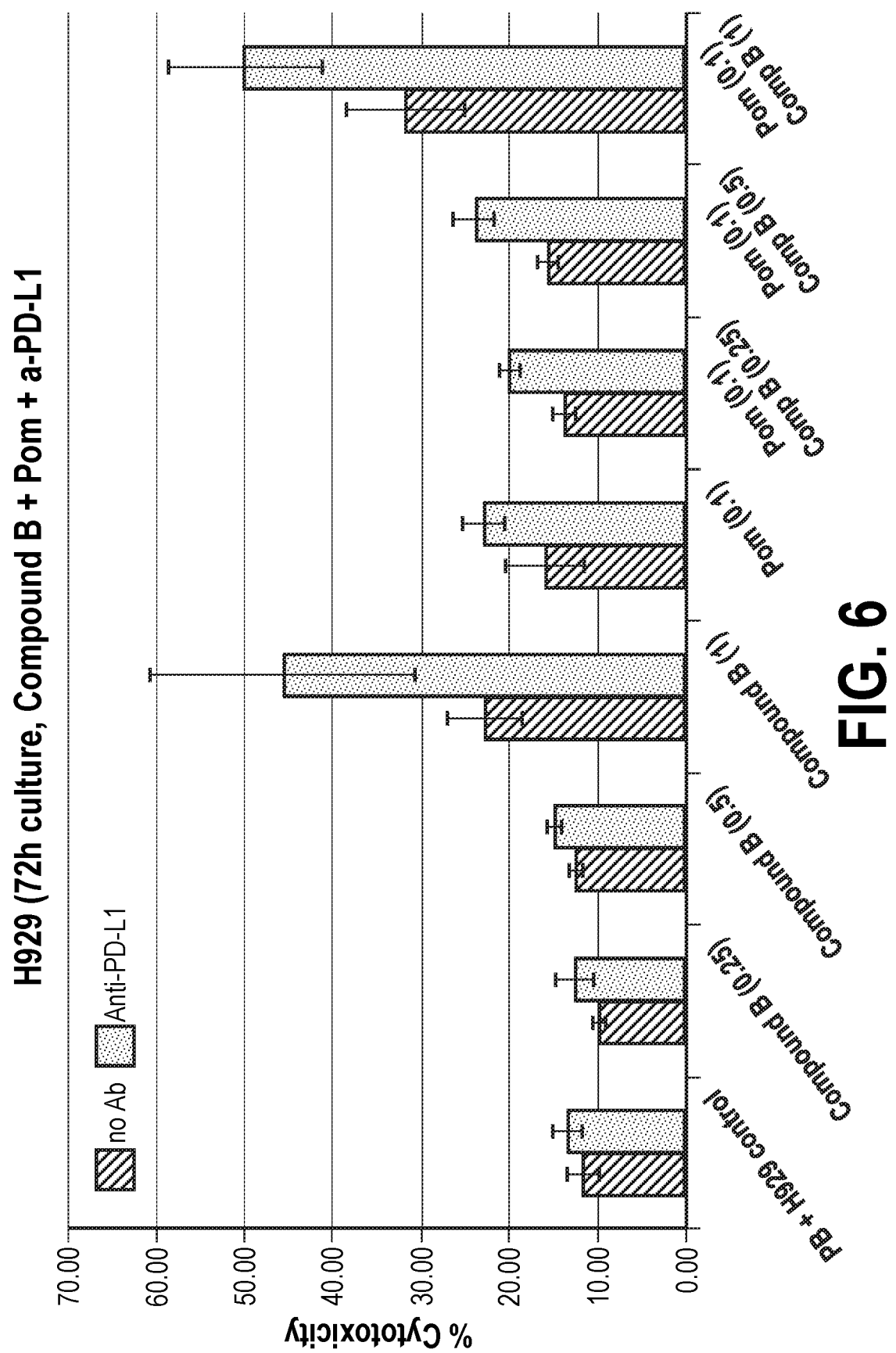
FIG. 6 is a bar graph showing the effect of Compound B in combination with pomalidomide on anti-PD-L1 antibody induced cell mediated cytotoxicity in H929 cells.

To assess the effect of Compound B in combination with pomalidomide on ADCC using anti-PD-L1 antibody-dependent cell-mediated cytotoxicity in H929 cells, H929 cells were stained with carboxyfluorescein succinimidyl ester (CFSE) and cultured with PBMCs in the presence or absence of pomalidomide (0.1 µM), Compound B (0.25, 0.5, 1 µM) for 72 hours. The cells were then incubated with anti-PD-L1 antibody (0.5 µg/ml PD-L1) for 3 hours. Cytotoxicity was assessed by FCM. Compound B combined with pomalidomide enhanced ADCC (FIG. 6). Similarly, Compound B alone enhanced anti-PD-L1 Ab-induced cytotoxicity in H929.

Figure 7:
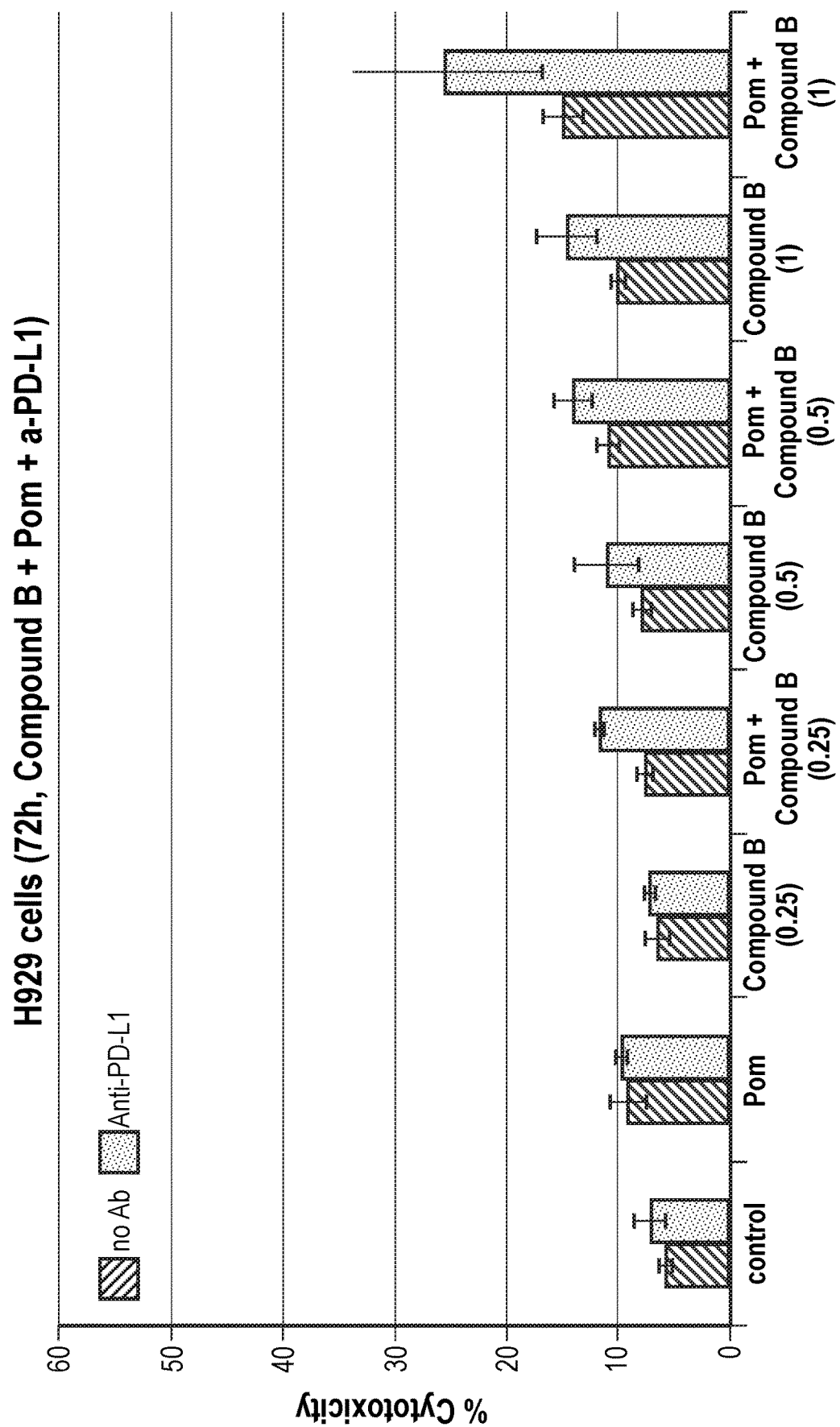
FIG. 7 is a bar graph showing the effect of pomalidomide (alone), Compound B (alone), or pomalidomide in combination with Compound B on anti-PD-L1 dependent cell-mediated cytotoxicity in H929 cells.
Figure 8:
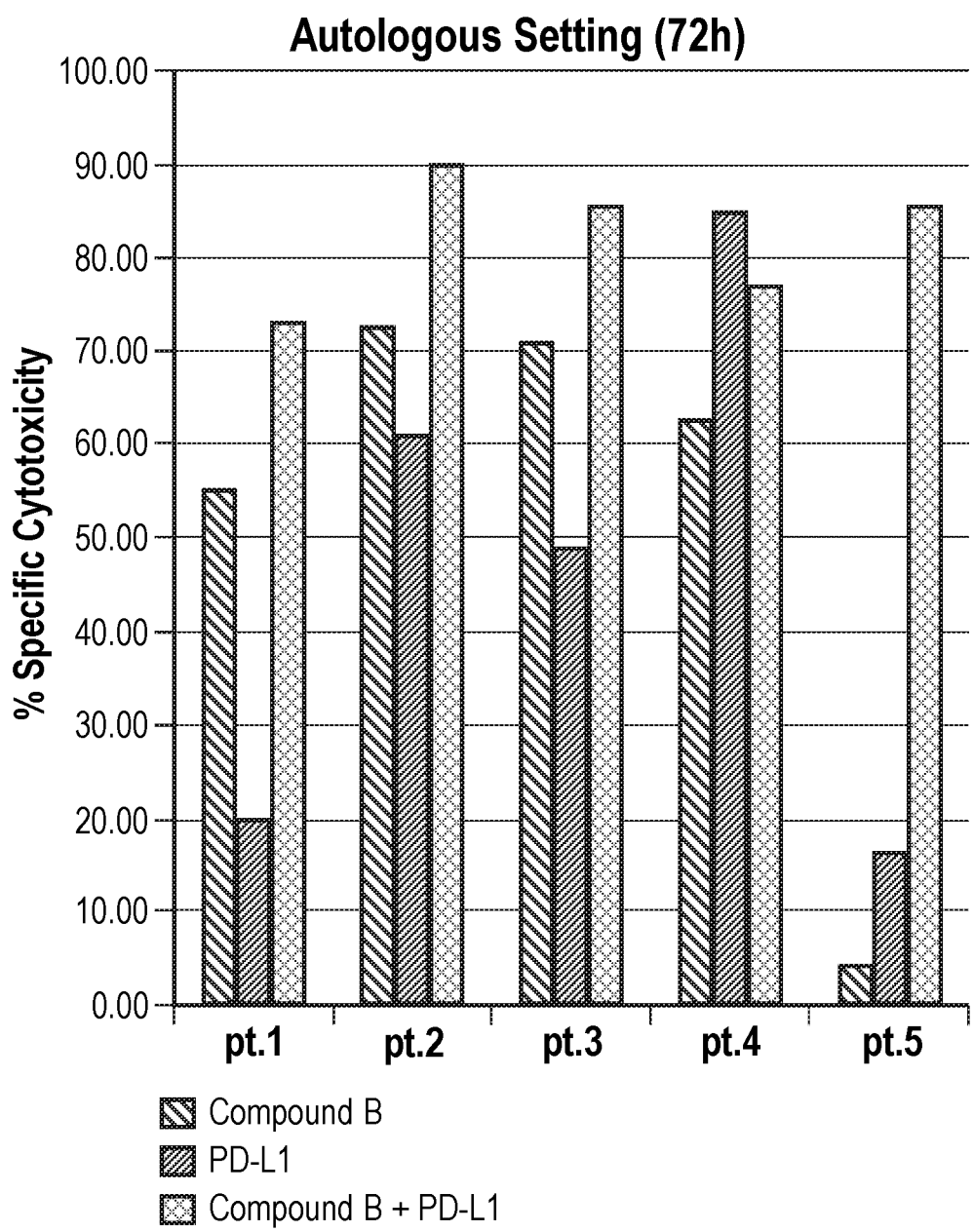
FIG. 8 and FIG. 9 are bar graphs showing the effect of Compound B on anti-PD-L1 antibody dependent cell mediated cytotoxicity in mononuclear cells from multiple myeloma patients' bone marrow aspirates. The average cytotoxicity (mean±SD) was calculated from 5 patients' samples.
Figure 9:
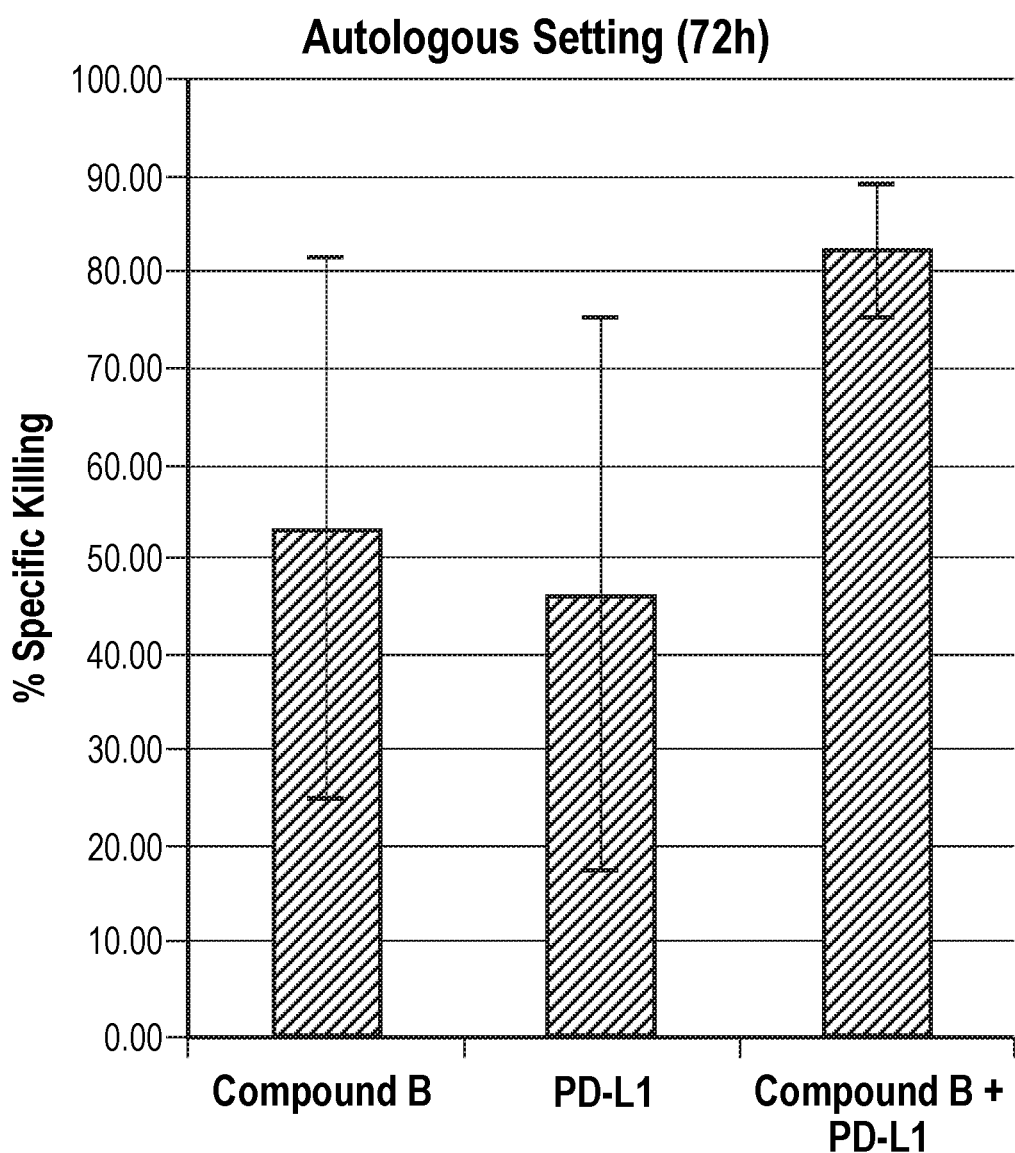

H929 cells were stained with CFSE and cultured with PBMCs in the presence or absence of pomalidomide (0.1 µM), Compound B (0.25, 0.5, 1 µM) for 72 h. The cells were then incubated with Ab (0.5 µg/ml PD-L1) for 3 h. Cytotoxicity was assessed by FCM (FIG. 7). Compound B also enhanced anti-PD-L1 antibody induced-cytotoxicity in an autologous setting. Mononuclear cells from MM patients' bone marrow aspirates were cultured with anti-PD-L1 Ab (0.5 µg/ml) with or without Compound B (0.5 µM) for 72 h (FIG. 8 and FIG. 9).

The invention claimed is:

1. A method for treating multiple myeloma in a subject in need thereof, comprising administering to the subject a therapeutically effective amount of
   a) a histone deacetylase 6 (HDAC6) inhibitor that is

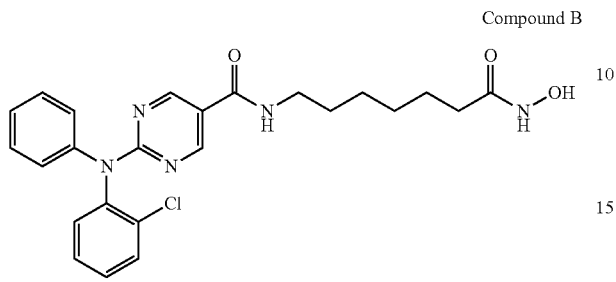

Compound B or a pharmaceutically acceptable salt thereof, and
   b) a programmed death ligand 1 (PD-L1) inhibitor that is MDX-1105 (BMS-936559), or a pharmaceutically acceptable salt thereof.

2. The method of claim 1, wherein the combination further comprises:
   c) pomalidomide, or a pharmaceutically acceptable salt thereof.

3. The method of claim 1 further comprising administering to the subject a therapeutically effective amount of dexamethasone.

* * * * *

SEQUENCE LISTING

```
<160> NUMBER OF SEQ ID NOS: 4

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gly Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
```

```
            65                  70                  75                  80
Met Glu Leu Ser Ser Leu Arg Ser Glu Asp Thr Ala Val Tyr Phe Cys
                    85                  90                  95
Ala Arg Lys Phe His Phe Val Ser Gly Ser Pro Phe Gly Asn Asp Val
                100                 105                 110
Gln Gly Gln Gly Thr Thr Val Thr Val Ser Ser Ala Ser Thr Lys Gly
                115                 120                 125
Pro Ser Val Phe Pro Leu Ala Pro Cys Ser Arg Ser Thr Ser Glu Ser
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Lys Thr Tyr Thr Cys Asn Val
                195                 200                 205
Asp His Lys Pro Ser Asn Thr Lys Val Asp Lys Arg Val Glu Ser Lys
            210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
                260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Gln Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
            435                 440                 445
Gly Lys
    450

<210> SEQ ID NO 2
<211> LENGTH: 214
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaccagcac actgagaatc aa                                                22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggaggatgt gccagaggt                                                    19
```